United States Patent
Weiss

(10) Patent No.: US 10,138,284 B2
(45) Date of Patent: *Nov. 27, 2018

(54) NON-STANDARD INSULIN ANALOGUES

(71) Applicant: CASE WESTERN RESERVE UNIVERSITY, Cleveland, OH (US)

(72) Inventor: Michael A. Weiss, Cleveland, OH (US)

(73) Assignee: Case Western Reserve University, Cleveland, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/277,319

(22) Filed: Sep. 27, 2016

(65) Prior Publication Data

US 2017/0101456 A1 Apr. 13, 2017

Related U.S. Application Data

(63) Continuation of application No. 14/232,496, filed as application No. PCT/US2012/046575 on Jul. 13, 2012, now Pat. No. 9,487,572.

(60) Provisional application No. 61/507,324, filed on Jul. 13, 2011.

(51) Int. Cl.
   *C07K 14/62* (2006.01)

(52) U.S. Cl.
   CPC .................... *C07K 14/62* (2013.01)

(58) Field of Classification Search
   None
   See application file for complete search history.

(56) References Cited

U.S. PATENT DOCUMENTS

| 5,514,646 A | 5/1996 | Chance et al. |
| 6,221,633 B1 * | 4/2001 | Ertl .................. C07K 14/62 435/243 |

FOREIGN PATENT DOCUMENTS

| WO | WO 2009129250 A2 * | 10/2009 | ............. C07K 14/62 |
| WO | 2010014946 A1 | 2/2010 | |
| WO | 2101080607 A1 | 7/2010 | |
| WO | 2011072288 A2 | 6/2011 | |

OTHER PUBLICATIONS

PCT/US2012/04657 International Search Report and Written Opinion, dated Jan. 13, 2014.

Nomura, Kamada, Ito, Sakamot, Chuman, Ishimor, Shimohigashi, Sakaguchi, "Probing Phenylalnine Environments in Oligomeric Structures with Pentafluorophenylalanine and Cyclohexylalanine", Bioplolymers vol. 95, No. 6, Jan. 28, 2011, pp. 410-419, published online at Wiley Online Library (wileyonlinelibrary.com).

* cited by examiner

*Primary Examiner* — Rachael E Bredefeld
*Assistant Examiner* — Erinne R Dabkowski
(74) *Attorney, Agent, or Firm* — Hahn Loeser & Parks, LLP; John J. Cunniff

(57) ABSTRACT

An insulin analog comprises a B-chain polypeptide containing a cyclohexanylalanine substitution at position B24 and optionally containing additional amino-acid substitutions at positions A8, B28, and/or B29. A proinsulin analog or single-chain insulin analog containing a B domain containing a cyclohexanylalanine substitution at position B24 and optionally containing additional amino-acid substitutions at positions A8, B28, and/or B29. The analog may be an analog of a mammalian insulin, such as human insulin. A nucleic acid encoding such an insulin analog is also provided. A method of lowering the blood sugar of a patient comprises administering a physiologically effective amount of the insulin analog or a physiologically acceptable salt thereof to a patient. A method of semi-synthesis using an unprotected octapeptide by means of modification of an endogenous tryptic site by non-standard amino-acid substitutions.

4 Claims, 9 Drawing Sheets
Specification includes a Sequence Listing.

PROINSULIN

MODEL planar (aromatic)

non-planar (aliphatic)

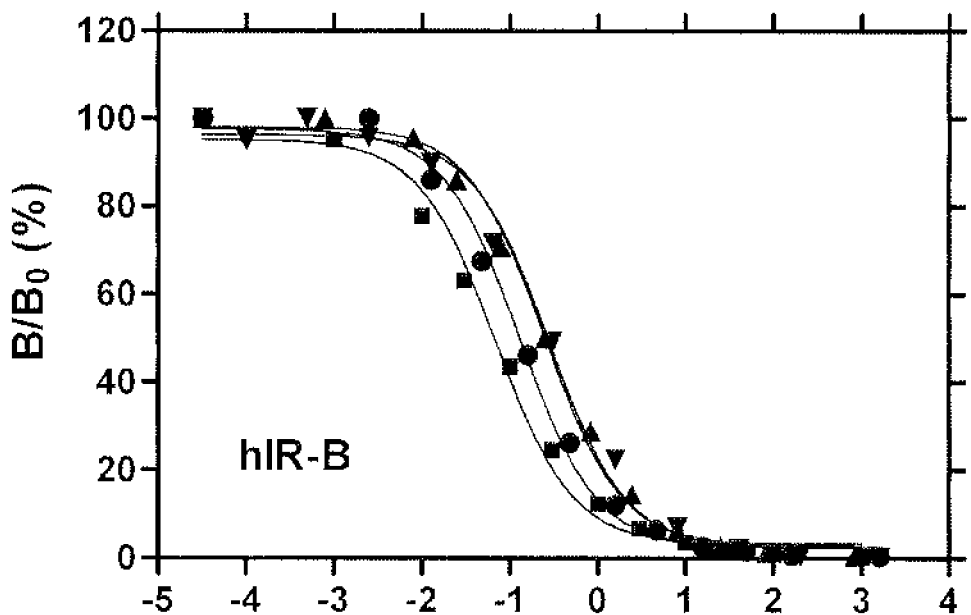
FIG. 6A
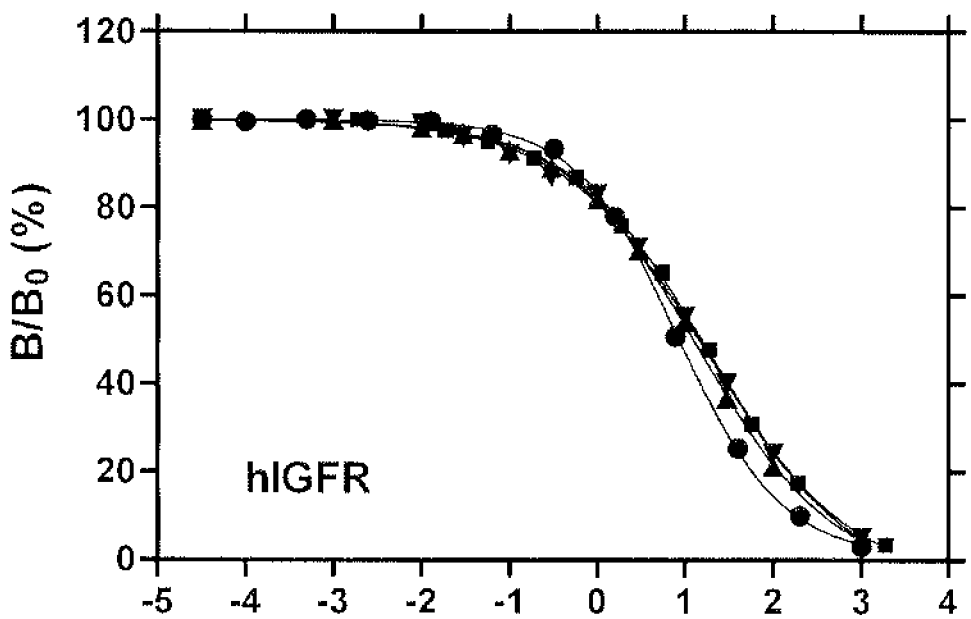
FIG. 6B log[insulin (nM)]

SEQUENCE LISTING

```
<160> NUMBER OF SEQ ID NOS: 23

<210> SEQ ID NO 1
<211> LENGTH: 86
<212> TYPE: PRT
<213> ORGANISM: Homo sapien

<400> SEQUENCE: 1

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30

Glu Ala Glu Asp Leu Gln Val Gly Gln Val Glu Leu Gly Gly Gly Pro
        35                  40                  45

Gly Ala Gly Ser Leu Gln Pro Leu Ala Leu Glu Gly Ser Leu Gln Lys
    50                  55                  60

Arg Gly Ile Val Glu Gln Cys Cys Thr Ser Ile Cys Ser Leu Tyr Gln
65                  70                  75                  80

Leu Glu Asn Tyr Cys Asn
                85

<210> SEQ ID NO 2
<211> LENGTH: 21
<212> TYPE: PRT
<213> ORGANISM: Homo sapiens

<400> SEQUENCE: 2

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 3
<211> LENGTH: 30
<212> TYPE: PRT
<213> ORGANISM: Homo sapiens

<400> SEQUENCE: 3

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 4
<211> LENGTH: 30
<212> TYPE: PRT
<213> ORGANISM: Homo sapiens
<220> FEATURE:
<221> NAME/KEY: MISC_FEATURE
<222> LOCATION: (10)..(10)
<223> OTHER INFORMATION: Xaa is His or Asp
<220> FEATURE:
```

```
<221> NAME/KEY: MISC_FEATURE
<222> LOCATION: (24)..(24)
<223> OTHER INFORMATION: Xaa is Cyclohexanylalanine
<220> FEATURE:
<221> NAME/KEY: MISC_FEATURE
<222> LOCATION: (28)..(28)
<223> OTHER INFORMATION: Xaa is Asp, Pro, Lys or Arg
<220> FEATURE:
<221> NAME/KEY: MISC_FEATURE
<222> LOCATION: (29)..(29)
<223> OTHER INFORMATION: Xaa is Lys or Pro

<400> SEQUENCE: 4

Phe Val Asn Gln His Leu Cys Gly Ser Xaa Leu Val Glu Ala Leu Tyr
1               5                  10                  15

Leu Val Cys Gly Glu Arg Gly Xaa Phe Tyr Thr Xaa Xaa Thr
            20                  25                  30

<210> SEQ ID NO 5
<211> LENGTH: 30
<212> TYPE: PRT
<213> ORGANISM: Homo sapiens
<220> FEATURE:
<221> NAME/KEY: MISC_FEATURE
<222> LOCATION: (10)..(10)
<223> OTHER INFORMATION: Xaa is His or Asp
<220> FEATURE:
<221> NAME/KEY: MISC_FEATURE
<222> LOCATION: (24)..(24)
<223> OTHER INFORMATION: Xaa is Cyclohexanylalanine
<220> FEATURE:
<221> NAME/KEY: MISC_FEATURE
<222> LOCATION: (29)..(29)
<223> OTHER INFORMATION: Xaa is Asp, Pro, ornithine, diaminobutyric
      acid, diaminoproprionic acid, norleucine, aminobutric acid, or
      aminoproprionic acid

<400> SEQUENCE: 5

Phe Val Asn Gln His Leu Cys Gly Ser Xaa Leu Val Glu Ala Leu Tyr
1               5                  10                  15

Leu Val Cys Gly Glu Arg Gly Xaa Phe Tyr Thr Pro Xaa Thr
            20                  25                  30

<210> SEQ ID NO 6
<211> LENGTH: 30
<212> TYPE: PRT
<213> ORGANISM: Homo sapiens
<220> FEATURE:
<221> NAME/KEY: MISC_FEATURE
<222> LOCATION: (24)..(24)
<223> OTHER INFORMATION: Xaa is Cyclohexanylalanine

<400> SEQUENCE: 6

Phe Val Asn Gln His Leu Cys Gly Ser His Leu Val Glu Ala Leu Tyr
1               5                  10                  15

Leu Val Cys Gly Glu Arg Gly Xaa Phe Tyr Thr Lys Pro Thr
            20                  25                  30

<210> SEQ ID NO 7
<211> LENGTH: 30
<212> TYPE: PRT
<213> ORGANISM: Homo sapiens
<220> FEATURE:
<221> NAME/KEY: MISC_FEATURE
<222> LOCATION: (24)..(24)
<223> OTHER INFORMATION: Xaa is Cyclohexanylalanine

<400> SEQUENCE: 7

Phe Val Asn Gln His Leu Cys Gly Ser His Leu Val Glu Ala Leu Tyr
```

```
            1               5                   10                  15
            Leu Val Cys Gly Glu Arg Gly Xaa Phe Tyr Thr Asp Lys Thr
                            20                  25                  30
```

<210> SEQ ID NO 8
<211> LENGTH: 86
<212> TYPE: PRT
<213> ORGANISM: homosapien
<220> FEATURE:
<221> NAME/KEY: MISC_FEATURE
<222> LOCATION: (1)..(1)
<223> OTHER INFORMATION: Xaa is His or Phe
<220> FEATURE:
<221> NAME/KEY: MISC_FEATURE
<222> LOCATION: (24)..(24)
<223> OTHER INFORMATION: Xaa is Cyclohexanylalanine
<220> FEATURE:
<221> NAME/KEY: MISC_FEATURE
<222> LOCATION: (26)..(26)
<223> OTHER INFORMATION: Xaa is Tyr or Phe
<220> FEATURE:
<221> NAME/KEY: MISC_FEATURE
<222> LOCATION: (28)..(28)
<223> OTHER INFORMATION: Xaa is Pro, Lys or Asp
<220> FEATURE:
<221> NAME/KEY: MISC_FEATURE
<222> LOCATION: (29)..(29)
<223> OTHER INFORMATION: Xaa is Lys or Pro
<220> FEATURE:
<221> NAME/KEY: MISC_FEATURE
<222> LOCATION: (31)..(65)
<223> OTHER INFORMATION: Xaa is 0-35 of any amino acid or a break in the
      amino acid chain
<220> FEATURE:
<221> NAME/KEY: MISC_FEATURE
<222> LOCATION: (69)..(69)
<223> OTHER INFORMATION: Xaa is His or Glu
<220> FEATURE:
<221> NAME/KEY: MISC_FEATURE
<222> LOCATION: (73)..(73)
<223> OTHER INFORMATION: Xaa is His or Thr

<400> SEQUENCE: 8

```
Xaa Val Asn Gln His Leu Cys Gly Ser His Leu Val Glu Ala Leu Tyr
1               5                   10                  15

Leu Val Cys Gly Glu Arg Gly Xaa Phe Xaa Thr Xaa Xaa Thr Xaa Xaa
                20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Gly Ile Val Xaa Gln Cys Cys Xaa Ser Ile Cys Ser Leu Tyr Gln
65                  70                  75                  80

Leu Glu Asn Tyr Cys Asn
                85
```

<210> SEQ ID NO 9
<211> LENGTH: 30
<212> TYPE: PRT
<213> ORGANISM: Homo sapiens
<220> FEATURE:
<221> NAME/KEY: MISC_FEATURE
<222> LOCATION: (24)..(24)
<223> OTHER INFORMATION: Xaa is Cyclohexanylalanine

<400> SEQUENCE: 9

```
Phe Val Lys Gln His Leu Cys Gly Ser His Leu Val Glu Ala Leu Tyr
1               5                   10                  15
```

Leu Val Cys Gly Glu Arg Gly Xaa Phe Tyr Thr Pro Glu Thr
            20                  25                  30

<210> SEQ ID NO 10
<211> LENGTH: 22
<212> TYPE: PRT
<213> ORGANISM: Homo sapiens
<220> FEATURE:
<221> NAME/KEY: MISC_FEATURE
<222> LOCATION: (10)..(10)
<223> OTHER INFORMATION: Xaa is His or Asp

<400> SEQUENCE: 10

Phe Val Asn Gln His Leu Cys Gly Ser Xaa Leu Val Glu Ala Leu Tyr
1               5                   10                  15

Leu Val Cys Gly Glu Arg
            20

<210> SEQ ID NO 11
<211> LENGTH: 8
<212> TYPE: PRT
<213> ORGANISM: Homo sapiens

<400> SEQUENCE: 11

Gly Phe Phe Tyr Thr Pro Lys Thr
1               5

<210> SEQ ID NO 12
<211> LENGTH: 8
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is Phe or Cyclohexanylalanine

<400> SEQUENCE: 12

Gly Xaa Phe Tyr Thr Pro Lys Thr
1               5

<210> SEQ ID NO 13
<211> LENGTH: 8
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is Phe or Cyclohexanylalanine
<220> FEATURE:
<221> NAME/KEY: MISC_FEATURE
<222> LOCATION: (7)..(7)
<223> OTHER INFORMATION: Xaa is Ornithine

<400> SEQUENCE: 13

Gly Xaa Phe Tyr Thr Pro Xaa Thr
1               5

<210> SEQ ID NO 14
<211> LENGTH: 8
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is Phe or Cyclohexanylalanine
<220> FEATURE:
<221> NAME/KEY: MISC_FEATURE
<222> LOCATION: (7)..(7)
<223> OTHER INFORMATION: Xaa is Norleucine

<400> SEQUENCE: 14

Gly Xaa Phe Tyr Thr Pro Xaa Thr
1               5

<210> SEQ ID NO 15
<211> LENGTH: 90
<212> TYPE: DNA
<213> ORGANISM: Homo sapiens

<400> SEQUENCE: 15
tttgtgaacc aacacctgtg cggctcacac ctggtggaag ctctctacct agtgtgcggg    60
gaacgaggct agttctacac acccaagacc                                    90

<210> SEQ ID NO 16
<211> LENGTH: 90
<212> TYPE: DNA
<213> ORGANISM: Homo sapiens

<400> SEQUENCE: 16
tttgttaacc aacatttgtg tggttctcat ttggttgaag ctttgtactt ggtttgtggt    60
gaaagaggtt agttttacac tccaaagact                                    90

<210> SEQ ID NO 17
<211> LENGTH: 261
<212> TYPE: DNA
<213> ORGANISM: Homo sapiens

<400> SEQUENCE: 17
tttgtgaacc aacacctgtg cggctcacac ctggtggaag ctctctacct agtgtgcggg    60
gaacgaggct agttctacac acccaagacc cgccggagg cagaggacct gcaggtgggg    120
caggtggagc tgggcggcgg ccctggtgca ggcagcctgc agcccttggc cctggagggg   180
tccctgcaga agcgtggcat tgtggaacaa tgctgtacca gcatctgctc cctctaccag   240
ctggagaact actgcaacta g                                             261

<210> SEQ ID NO 18
<211> LENGTH: 261
<212> TYPE: DNA
<213> ORGANISM: homosapien

<400> SEQUENCE: 18
tttgttaacc aacatttgtg tggttctcat ttggttgaag ctttgtactt ggtttgtggt    60
gaaagaggtt agttttacac tccaaagact agaagagaag ctgaagattt gcaagttggt   120
caagttgaat tgggtggtgg tccaggtgct ggttctttgc aaccattggc tttggaaggt   180
tctttgcaaa agagaggtat tgttgaacaa tgttgtactt ctatttgttc tttgtaccaa   240
ttggaaaact actgtaacta a                                             261

<210> SEQ ID NO 19
<211> LENGTH: 21
<212> TYPE: PRT
<213> ORGANISM: Homo sapiens

<400> SEQUENCE: 19

Gly Ile Val Glu Gln Cys Cys Glu Ser Ile Cys Ser Leu Tyr Gln Leu
1               5                   10                  15

Glu Asn Tyr Cys Asn
            20

```
<210> SEQ ID NO 20
<211> LENGTH: 30
<212> TYPE: PRT
<213> ORGANISM: Homo sapiens

<400> SEQUENCE: 20

Phe Val Asn Gln His Leu Cys Gly Ser His Leu Val Glu Ala Leu Tyr
1               5                   10                  15

Leu Val Cys Gly Glu Arg Gly Phe Phe Tyr Thr Lys Pro Thr
            20                  25                  30

<210> SEQ ID NO 21
<211> LENGTH: 30
<212> TYPE: PRT
<213> ORGANISM: Homo sapiens
<220> FEATURE:
<221> NAME/KEY: MISC_FEATURE
<222> LOCATION: (24)..(24)
<223> OTHER INFORMATION: Xaa is Cyclohexanylalanine

<400> SEQUENCE: 21

Phe Val Asn Gln His Leu Cys Gly Ser Asp Leu Val Glu Ala Leu Tyr
1               5                   10                  15

Leu Val Cys Gly Glu Arg Gly Xaa Phe Tyr Thr Lys Pro Thr
            20                  25                  30

<210> SEQ ID NO 22
<211> LENGTH: 30
<212> TYPE: PRT
<213> ORGANISM: Homo sapien
<220> FEATURE:
<221> NAME/KEY: MISC_FEATURE
<222> LOCATION: (25)..(25)
<223> OTHER INFORMATION: Xaa is Cyclohexanylalanine

<400> SEQUENCE: 22

Phe Val Asn Gln His Leu Cys Gly Ser Asp Leu Val Glu Ala Leu Tyr
1               5                   10                  15

Leu Val Cys Gly Glu Arg Gly Phe Xaa Tyr Thr Lys Pro Thr
            20                  25                  30

<210> SEQ ID NO 23
<211> LENGTH: 8
<212> TYPE: PRT
<213> ORGANISM: Homo sapien

<400> SEQUENCE: 23

Asp Tyr Lys Asp Asp Asp Asp Lys
1               5
```

NON-STANDARD INSULIN ANALOGUES

CROSS REFERENCE TO RELATED APPLICATIONS

This application is a continuation of U.S. application Ser. No. 14/232,496, filed Jan. 13, 2014, and granted a filing date of Jun. 12, 2014 under 35 U.S.C. § 371, which is a national stage of PCT/US2012/046575, filed Jul. 13, 2012, which claims the benefit of U.S. Provisional Application No. 61/507,324 filed on Jul. 13, 2011.

STATEMENT REGARDING FEDERALLY SPONSORED RESEARCH OR DEVELOPMENT

This invention was made with government support under grants DK040949 and DK074176 awarded by the National Institutes of Health (NIH). The government has certain rights in the invention.

THE NAMES OF THE PARTIES TO A JOINT RESEARCH AGREEMENT

The subject matter of the instant application was developed and the claimed invention was made by or on behalf of a party to a joint research agreement between inventor Michael A. Weiss and Thermalin Diabetes, LLC. The joint research agreement was in effect prior to and at the time of invention of the subject matter of the instant application.

BACKGROUND OF THE INVENTION

This invention relates to polypeptide hormone analogues that exhibits enhanced pharmaceutical properties, such as more rapid pharmacokinetics and/or augmented resistance to thermal fibrillation above room temperature. More particularly, this invention relates to insulin analogues that are modified by the incorporation of non-standard amino acids. Such non-standard sequences may optionally contain standard amino-acid substitutions at other sites in the A or B chains of an insulin analogue.

The engineering of non-standard proteins, including therapeutic agents and vaccines, may have broad medical and societal benefits. An example of a medical benefit would be optimization of the pharmacokinetic properties of a protein. An example of a further societal benefit would be the engineering of proteins more refractory than standard proteins with respect to degradation at or above room temperature for use in regions of the developing world where electricity and refrigeration are not consistently available. An example of a therapeutic protein is provided by insulin. Analogues of insulin containing non-standard amino-acid substitutions may in principle exhibit superior properties with respect to pharmacokinetics or resistance to thermal degradation. The challenge posed by the pharmacokinetics of insulin absorption following subcutaneous injection affects the ability of patients to achieve tight glycemic control and constrains the safety and performance of insulin pumps. The challenge posed by its physical degradation is deepened by the pending epidemic of diabetes mellitus in Africa and Asia. These issues are often coupled as modifications known in the art to accelerate absorption following subcutaneous injection usually worsen the resistance of insulin to chemical and/or physical degradation. Because fibrillation poses the major route of degradation above room temperature, the design of fibrillation-resistant formulations may enhance the safety and efficacy of insulin replacement therapy in such challenged regions. The present invention pertains to the use of a particular class of non-standard amino acids—an aliphatic ring system as exemplified by Cyclohexanylalanine (Cha)—to modify and improve distinct properties of insulin. During the past decade specific chemical modifications to the insulin molecule have been described that selectively modify one or another particular property of the protein to facilitate an application of interest. Whereas at the beginning of the recombinant DNA era (1980) wild-type human insulin was envisaged as being optimal for use in diverse therapeutic contexts, the broad clinical use of insulin analogues in the past decade suggests that a suite of non-standard analogs, each tailored to address a specific unmet need, would provide significant medical and societal benefits. Substitution of one natural amino acid at a specific position in a protein by another natural amino acid is well known in the art and is herein designated a standard substitution. Non-standard substitutions in insulin offer the prospect of accelerated absorption without worsening of the resistance to degradation.

Administration of insulin has long been established as a treatment for diabetes mellitus. Insulin is a small globular protein that plays a central role in metabolism in vertebrates. Insulin contains two chains, an A chain, containing 21 residues, and a B chain containing 30 residues. The hormone is stored in the pancreatic β-cell as a $Zn^{2+}$-stabilized hexamer, but functions as a $Zn^{2+}$-free monomer in the bloodstream. Insulin is the product of a single-chain precursor, proinsulin, in which a connecting region (35 residues) links the C-terminal residue of B chain (residue B30) to the N-terminal residue of the A chain (FIG. 1A). Although the structure of proinsulin has not been determined, a variety of evidence indicates that it consists of an insulin-like core and disordered connecting peptide (FIG. 1B). Formation of three specific disulfide bridges (A6-A11, A7-B7, and A20-B19; FIGS. 1A and 1B) is thought to be coupled to oxidative folding of proinsulin in the rough endoplasmic reticulum (ER). Proinsulin assembles to form soluble $Zn^{2+}$-coordinated hexamers shortly after export from ER to the Golgi apparatus. Endoproteolytic digestion and conversion to insulin occurs in immature secretory granules followed by morphological condensation. Crystalline arrays of zinc insulin hexamers within mature storage granules have been visualized by electron microscopy (EM). The sequence of insulin is shown in schematic form in FIG. 1C. Individual residues are indicated by the identity of the amino acid (typically using a standard three-letter code), the chain and sequence position (typically as a superscript).

Aromatic side chains in insulin, as in globular proteins in general, may engage in a variety of hydrophobic and weakly polar interactions, involving not only neighboring aromatic rings but also other sources of positive- or negative electrostatic potential. Examples include main-chain carbonyl- and amide groups in peptide bonds. Hydrophobic packing of aromatic side chains can occur within the core of proteins and at non-polar interfaces between proteins. Such aromatic side chains can be conserved among vertebrate proteins, reflecting their key contributions to structure or function. An example of a natural aromatic amino acid is phenylalanine. Its aromatic ring system contains six carbons arranged as a planar hexagon. Aromaticity is a collective property of the binding arrangement among these six carbons, leading to π electronic orbitals above and below the plane of the ring. These faces exhibit a partial negative electrostatic potential whereas the edge of the ring, containing five C—H moieties, exhibits a partial positive electrostatic potential. This asymmetric distribution of partial charges gives rise to a quadrapole electrostatic moment and may participate in weakly polar interactions with other formal or partial charges in a protein. An additional characteristic feature of an aromatic side chains is its volume. Determinants of this volume include the topographic contours of its five C—H moieties at the edges of the planar ring. Substitution of an aromatic ring system by a corresponding aliphatic ring system would increase side-chain volume with loss of planarity and gain of one additional hydrogen atom at each carbon site (e.g., substitution of each C—H element with trigonal hybridization by $CH_2$ with tetrahedral hybridization).

An example of a conserved aromatic residue in a therapeutic protein is provided by phenylalanine at position B24 of the B chain of insulin (designated $Phe^{B24}$). This is one of three phenylalanine residues in insulin (positions B1, B24, and B25). A structurally similar tyrosine is at position B26. The structural environment of $Phe^{B24}$ in an insulin monomer is shown in a ribbon model (FIG. 1D) and in a space-filling model (FIG. 1E). Conserved among vertebrate insulins and insulin-like growth factors, the aromatic ring of $Phe^{B24}$ packs against (but not within) the hydrophobic core to stabilize the super-secondary structure of the B-chain. $Phe^{B24}$ lies at the classical receptor-binding surface and has been proposed to direct a change in conformation on receptor binding.

The pharmacokinetic features of insulin absorption after subcutaneous injection have been found to correlate with the rate of disassembly of the insulin hexamer. Although not wishing the present invention to be constrained by theory, modifications to the insulin molecule that lead to accelerated disassembly of the insulin hexamer are thought to promote more rapid absorption of insulin monomers and dimers from the subcutaneous depot into the bloodstream. $Phe^{B24}$ packs at the dimer interface of insulin and so at three interfaces of an insulin hexamer. Its structural environment in the insulin monomer differs from its structural environment at these interfaces. In particular, the surrounding volume available to the side chain of $Phe^{B24}$ is larger in the monomer than in the dimer or hexamer.

A major goal of insulin replacement therapy in patients with diabetes mellitus is tight control of the blood glucose concentration to prevent its excursion above or below the normal range characteristic of healthy human subjects. Excursions below the normal range are associated with immediate adrenergic or neuroglycopenic symptoms, which in severe episodes lead to convulsions, coma, and death. Excursions above the normal range are associated with increased long-term risk of microvascular disease, including retinapathy, blindness, and renal failure. Because the pharmacokinetics of absorption of wild-type human insulin following subcutaneous injection is often too slow and too prolonged relative to the physiological requirements of post-prandial metabolic homeostasis, considerable efforts have been expended during the past 20 years to develop insulin analogues that exhibit more rapid absorption with pharmacodynamic effects that are more rapid in onset and less prolonged in duration. Examples of such rapid-acting analogues known in the art are [$Lys^{B28}$, $Pro^{B29}$]-insulin (KP-insulin, the active component of Humalog®), [$Asp^{B28}$]-insulin (Novalog®), and [$Lys^{B3}$, $Glu^{B29}$]-insulin (Apidra®). Although widely used in clinical practice, these analogues exhibit two principal limitations. First, although their pharmacokinetic and pharmacodynamic profiles are more rapid than those of wild-type insulin, they are not rapid enough in many patients to optimize glycemic control or enable the safe and effective use of algorithm-based insulin pumps (closed-loop systems). Second, the amino-acid substitutions in these analogues impair the thermodynamic stability of insulin and exacerbate its susceptibility to fibrillation above room temperature. Thus, the safety, efficacy, and real-world convenience of these products have been limited by a trade-off between accelerated absorption and accelerated degradation.

Protein Engineering and the Mechanism of Insulin Absorption.

The major structural interface of the insulin hexamer is provided by an anti-parallel β-sheet at the dimerization surface. The component β-strands comprise residues B24-B28 and dimer-related residues B24'-B28'; this segment has the amino-acid sequence FFYTP (residues 24-28 of SEQ ID NO: 3). The core of the β-sheet is provided by the three aromatic side chains $Phe^{B24}$, $Phe^{B25}$, and $Tyr^{B26}$, which in the active insulin monomer also contact the insulin receptor. Substitutions known in the art to provide rapid-acting and active insulin analogues occur at positions B28 ($Pro^{B28}$ in wild-type insulin) and flanking site B29 ($Lys^{B29}$ in wild-type insulin). Standard amino-acid substitutions at core sites B24, B25, and B26 have not been employed in past design of insulin analogues intended for the treatment of patients with diabetes mellitus since such substitutions, as known in the art, typically impair biological activity. Substitution of $Phe^{B24}$ by Tyr, for example, impairs activity by more than twentyfold despite its seemingly conservative character. The importance of these invariant aromatic residues has been highlighted by the finding of genetic (germ-line) mutations at positions B24 and B25 that cause diabetes mellitus in human patients.

Fibrillation, which is a serious concern in the manufacture, storage and use of insulin and insulin analogues for the treatment of diabetes mellitus, is enhanced with higher temperature, lower pH, agitation, or the presence of urea, guanidine, ethanol co-solvent, or hydrophobic surfaces. Current US drug regulations demand that insulin be discarded if fibrillation occurs at a level of one percent or more. Because fibrillation is enhanced at higher temperatures, patients with diabetes mellitus optimally must keep insulin refrigerated prior to use. Fibrillation of insulin or an insulin analogue can be a particular concern for such patients utilizing an external insulin pump, in which small amounts of insulin or insulin analogue are injected into the patient's body at regular intervals. In such a usage, the insulin or insulin analogue is not kept refrigerated within the pump apparatus, and fibrillation of insulin can result in blockage of the catheter used to inject insulin or insulin analogue into the body, potentially resulting in unpredictable fluctuations in blood glucose levels or even dangerous hyperglycemia. At least one recent report has indicated that insulin Lispro (KP-insulin, an analogue in which residues B28 and B29 are interchanged relative to their positions in wild-type human insulin; trade name Humalog®) may be particularly susceptible to fibrillation and resulting obstruction of insulin pump catheters. Insulin exhibits an increase in degradation rate of 10-fold or more for each 10° C. increment in temperature above 25° C.; accordingly, guidelines call for storage at temperatures <30° C. and preferably with refrigeration.

The present theory of protein fibrillation posits that the mechanism of fibrillation proceeds via a partially folded intermediate state, which in turn aggregates to form an amyloidogenic nucleus. In this theory, it is possible that amino-acid substitutions that stabilize the native state may or may not stabilize the partially folded intermediate state and may or may not increase (or decrease) the free-energy barrier between the native state and the intermediate state. Therefore, the current theory indicates that the tendency of a given amino-acid substitution in the insulin molecule to increase or decrease the risk of fibrillation is highly unpredictable.

There is a need, therefore for an insulin analogue that displays more rapid hexamer disassembly while exhibiting at least a portion of the activity of the corresponding wild-type insulin and maintaining at least a portion of its chemical and/or physical stability.

SUMMARY OF THE INVENTION

It is, therefore, an aspect of the present invention to provide insulin analogues that provide more rapid hexamer disassembly and hence accelerated absorption following subcutaneous injection. The present invention addresses previous limitations for fast-acting insulin analogues, namely, that they still do not act sufficiently quickly to optimize glycemic control or enable use in implantable insulin pumps as they are more susceptible to fibrillation than wild-type insulin. The claimed invention circumvents previous design restrictions, including those regarding substitution of Phe$^{B24}$, through the incorporation of a non-standard amino-acid substitution at position B24. The non-standard amino-acid side chain (Cyclohexanylalanine at position B24; Cha$^{B24}$) markedly enhances rapidity of hexamer disassembly, the rate-limiting step in insulin absorption in humans. This is achieved by substitution of an aromatic amino-acid side chain by a non-aromatic analogue, which is non-planar but of approximately similar size and shape to Phenylalanine, where the analogue then maintains at least a portion of biological activity of the corresponding insulin or insulin analogue containing the native aromatic side chain.

In general, the present invention provides an insulin analogue comprising an insulin B-chain polypeptide containing at least one substitution selected from a cyclohexanylalanine substitution at position B24 and a substitution at position B29 selected from the group consisting of norleucine, aminobutyric acid, aminopropionic acid, omithine, diaminobutyric acid, and diaminopropionic acid. In another embodiment, the insulin analogue is a mammalian insulin analogue, such as an analogue of human insulin. In one embodiment, the insulin analogue additionally comprises substitution at position B28. In addition or in the alternative, an insulin analogue may optionally comprise a Glu substitution at position A8. In one particular set of embodiments, the B-chain polypeptide comprises an amino-acid sequence selected from the group consisting of SEQ. ID. NOS. 4-7, and 21 and polypeptides having three or fewer additional amino-acid substitutions thereof. In yet another particular set of embodiments, designated single-chain insulin analogs, the B-chain polypeptide is part of a single extended polypeptide of length 51-86 that comprises an amino-acid sequence provided in SEQ. ID. NO 8, and polypeptides having three or fewer additional amino-acid substitutions thereof.

In addition or in the alternative, the insulin analogue may contain a non-standard amino-acid substitution at position 29 of the B-chain. In one particular example, the non-standard amino acid at B29 is norleucine (Nle). In another particular example, the non-standard amino acid at B29 is omithine (Orn).

Also provided is a nucleic acid encoding an insulin analogue comprising a B-chain polypeptide that incorporates a non-standard amino acid at position B24 or B29 or both. In one example, the non-standard amino acid is encoded by a stop codon, such as the nucleic acid sequence TAG. An expression vector may comprise such a nucleic acid and a host cell may contain such an expression vector.

The invention also provides a method of lowering the blood sugar a patient. The method comprises administering a physiologically effective amount of an insulin analogue or a physiologically acceptable salt thereof to the patient, wherein the insulin analogue or a physiologically acceptable salt thereof contains a B-chain polypeptide incorporating a Cyclohexanylalanine as described above. In one embodiment, the Cyclohexanylalanine in the insulin analogue administered to a patient is located at position B24. In still another embodiment, the insulin analogue is a mammalian insulin analogue, such as an analogue of human insulin. In one particular set of embodiments, the B-chain polypeptide comprises an amino-acid sequence selected from the group consisting of SEQ. ID. NOS. 4-8, 21 and polypeptides having three or fewer additional amino-acid substitutions thereof.

BRIEF DESCRIPTION OF THE SEVERAL VIEWS OF THE DRAWINGS

FIG. 6A is a graph showing the results of receptor-binding studies of wild type human insulin (■), KP-insulin (●), Cha$^{B24}$-KP-insulin (▲) or Glu$^{A8}$-Cha$^{B24}$-KP-insulin (▼) using isolated insulin receptor (isoform B).

FIG. 6B is a graph showing the results of receptor-binding studies of wild type human insulin (■), KP-insulin (●), Cha$^{B24}$-KP-insulin (▲) or Glu$^{A8}$-Cha$^{B24}$-KP-insulin (▼) using human IGF-1 receptor.

DETAILED DESCRIPTION OF THE INVENTION

The present invention is directed an insulin analogue that provides a more rapid rate of hexamer disassembly where the analogue then maintains at least a portion of biological activity of the corresponding unmodified insulin or insulin analogue.

Figure 2A:
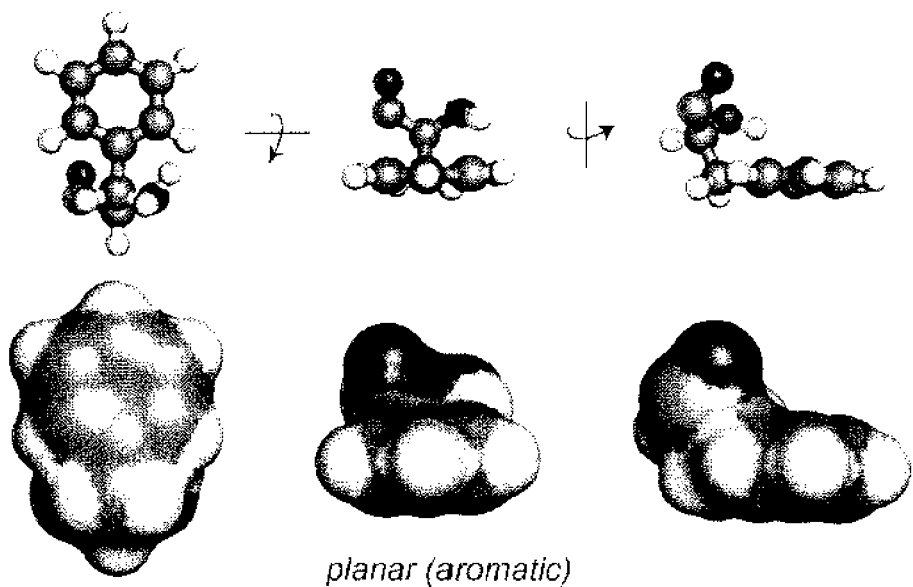
FIG. 2A is a series of ball and stick (top) and space-filling (bottom) representations of Phenylalanine (Phe).

The present invention pertains to non-standard modifications at position B24 to improve the properties of insulin with respect to rapidity of absorption following subcutaneous injection. In one instance the non-standard amino acid lacks aromaticity and its associated asymmetric distribution of partial positive and negative charges as demonstrated by substitution of the non-planar aliphatic ring system of cyclohexanylalanine. Loss of planarity in a non-aromatic ring system is associated with a change in its topographical contours and an increase in side-chain volume (FIG. 2B) relative to phenylalanine (FIG. 2A).

In one embodiment, the present invention provides an insulin analogue that provides more rapid hexamer disassembly by substitution of phenylalanine at position B24 by a non-standard amino acid. In one particular embodiment the more rapid hexamer disassembly is directed by substitution of cyclohexanylalanine at position B24. The present invention is not limited, however, to human insulin and its analogues. It is also envisioned that these substitutions may also be made in animal insulins such as porcine, bovine, equine, and canine insulins, by way of non-limiting examples.

It has also been discovered that Cha$^{B24}$-KP-insulin, when formulated in Lilly Diluent and following subcutaneous injection in a male Lewis rat rendered diabetic by streptozotocin, will direct a reduction in blood glucose concentration with a potency similar to that of KP-insulin in the same formulation.

In addition or in the alternative, the insulin analogue of the present invention may contain a non-standard amino-acid substitution at position 29 of the B chain, which is lysine (Lys) in wild-type insulin. In one particular example, the non-standard amino acid at B29 is norleucine (Nle). In another particular example, the non-standard amino acid at B29 is ornithine (Orn).

Furthermore, in view of the similarity between human and animal insulins, and use in the past of animal insulins in human patients with diabetes mellitus, it is also envisioned that other minor modifications in the sequence of insulin may be introduced, especially those substitutions considered "conservative." For example, additional substitutions of amino acids may be made within groups of amino acids with similar side chains, without departing from the present invention. These include the neutral hydrophobic amino acids: Alanine (Ala or A), Valine (Val or V), Leucine (Leu or L), Isoleucine (Ile or I), Proline (Pro or P), Tryptophan (Trp or W), Phenylalanine (Phe or F) and Methionine (Met or M). Likewise, the neutral polar amino acids may be substituted for each other within their group of Glycine (Gly or G), Serine (Ser or S), Threonine (Thr or T), Tyrosine (Tyr or Y), Cysteine (Cys or C), Glutamine (Glu or Q), and Asparagine (Asn or N). Basic amino acids are considered to include Lysine (Lys or K), Arginine (Arg or R) and Histidine (His or H). Acidic amino acids are Aspartic acid (Asp or D) and Glutamic acid (Glu or E). Unless noted otherwise or wherever obvious from the context, the amino acids noted herein should be considered to be L-amino acids.

Standard amino acids may also be substituted by non-standard amino acids belong to the same chemical class. By way of non-limiting example, the basic side chain Lys may be replaced by basic amino acids of shorter side-chain length (Ornithine, Diaminobutyric acid, or Diaminopropionic acid). Lys may also be replaced by the neutral aliphatic isostere Norleucine (Nle), which may in turn be substituted by analogues containing shorter aliphatic side chains (Aminobutyric acid or Aminopropionic acid).

In one example, the insulin analogue of the present invention contains three or fewer conservative substitutions other than the cyclic aliphatic substitution of the present invention.

Figure 2B:
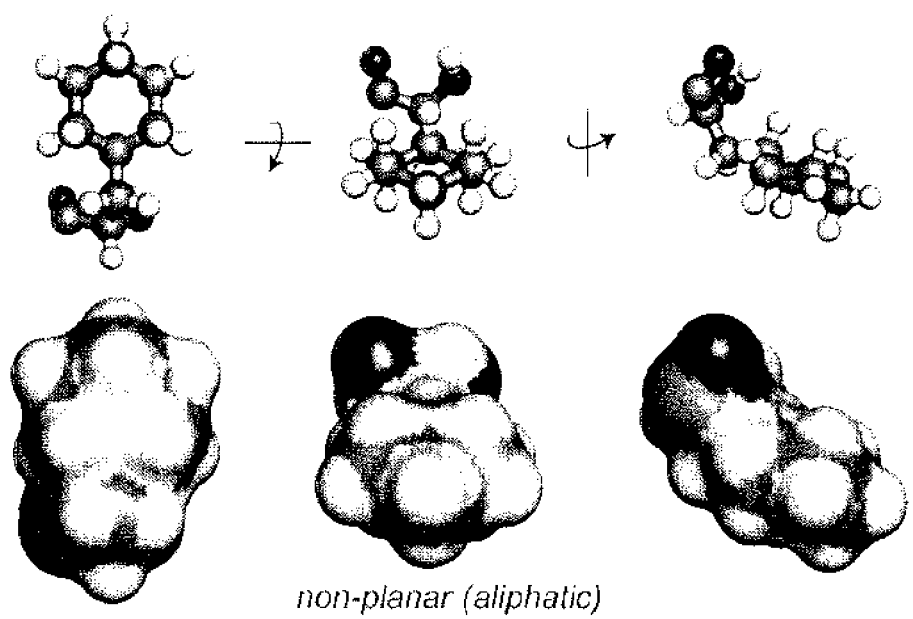
FIG. 2B is a series of ball and stick (top) and space-filling (bottom) representations of Cyclohexanylalanine (Cha).

As used in this specification and the claims, various amino acids in insulin or an insulin analogue may be noted by the amino-acid residue in question, followed by the position of the amino acid, optionally in superscript. The position of the amino acid in question includes the A- or B chain of insulin where the substitution is located. Thus, Phe$^{B24}$ denotes a phenylalanine at the twenty-fourth amino acid of the B chain of insulin. Unless noted otherwise or wherever obvious from the context, the location of substitutions should be understood to be relative to and in the context of human insulin. Aromatic and non-aromatic rings differ in planarity, reflecting the presence (Phe) or absence (Cha) of π electrons as illustrated in front and side views of Phenylalanine (FIG. 2A) relative to Cyclohexanylalanine (FIG. 2B).

Figure 3A:
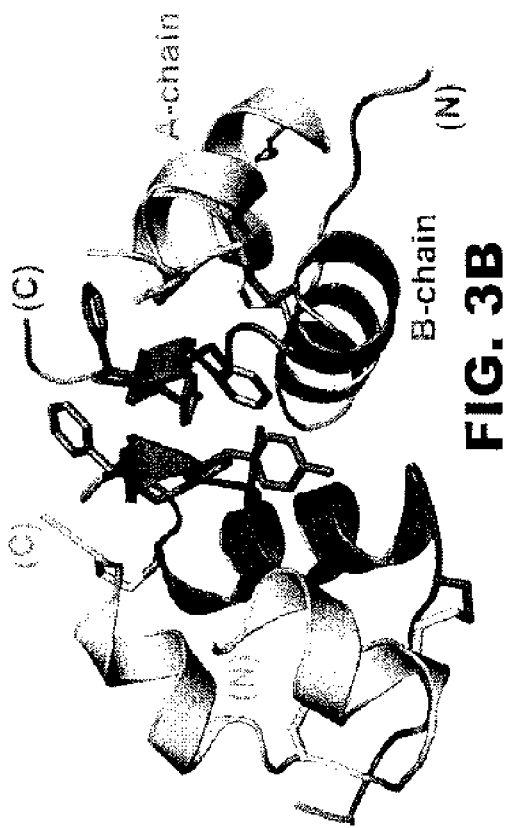
FIG. 3A is a structural model depicting the fit of Cha$^{B24}$ within the structure of wild-type insulin monomer.
Figure 3B:
FIG. 3B is a structural model depicting the fit of Cha$^{B24}$ within the structure of wild-type insulin dimer as extracted from the crystal structure of the T$_6$ zinc insulin hexamer (Protein Databank accession code 4INS)
Figure 3C:
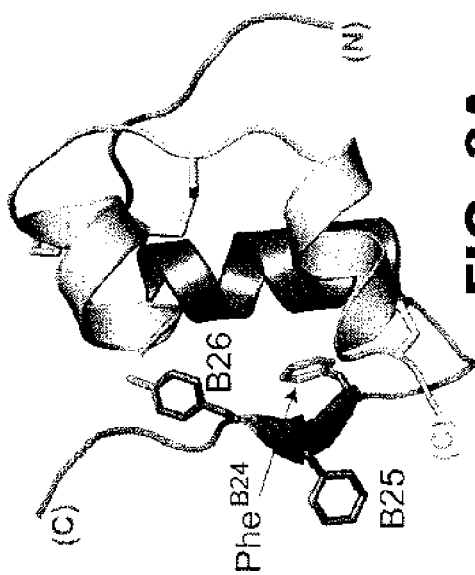
FIG. 3C is a structural model predicting the fit of Cyclohexanylalanine in the variant monomer.
Figure 3D:
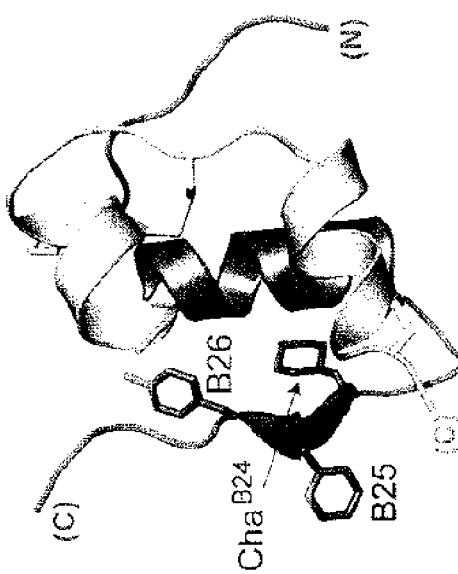
FIG. 3D is a structural model predicting the fit of Cyclohexanylalanine in the variant dimer.

Although not wishing to be constrained by theory, the present invention envisions that modifications at B24 that alter the weakly polar character of the ring system and/or enlarge its topographical contours would more readily be accommodated in the insulin monomer than at the dimer interface and so be associated with accelerated disassembly. In particular, because the dimer interface is characterized by multiple aromatic-aromatic interactions involving Phe$^{B24}$ and six other aromatic rings (Tyr$^{B16}$, Phe$^{B25}$, Tyr$^{B26}$, and their symmetry-related partners), the present invention further envisions that loss of aromaticity at position B24 would in general accelerate the disassembly of insulin hexamers and further accelerate the disassembly of variant hexamers containing destabilizing mutations elsewhere in the dimer- or trimer interface. Although the three-dimensional structure of a Cha$^{B24}$ variant of human insulin has not been determined, insight may be gained from rigid-body modeling based on the crystal structure of wild-type insulin (FIG. 3). A molecular model depicting the packing of Cha$^{B24}$ within an insulin monomer is shown in FIG. 3C relative to the wild-type Phe$^{B24}$ as shown in FIG. 3A. A molecular model depicting the packing of Cha$^{B24}$ within an insulin dimer interface is shown in FIG. 3D relative to the wild-type Phe$^{B24}$ as shown in FIG. 3A.

Figure 1A:
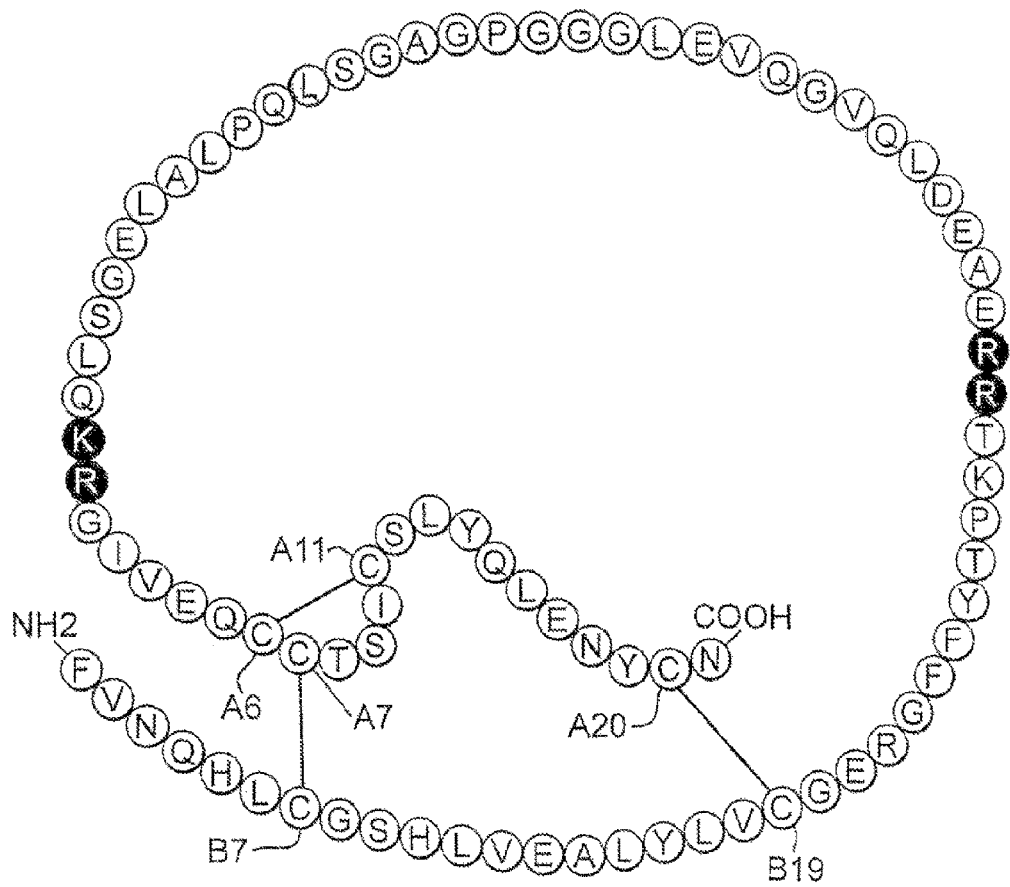
FIG. 1A is a schematic representation of the sequence of human proinsulin (SEQ ID NO:1) including the A- and B-chains and the connecting region shown with flanking dibasic cleavage sites (filled circles) and C-peptide (open circles).
Figure 1B:
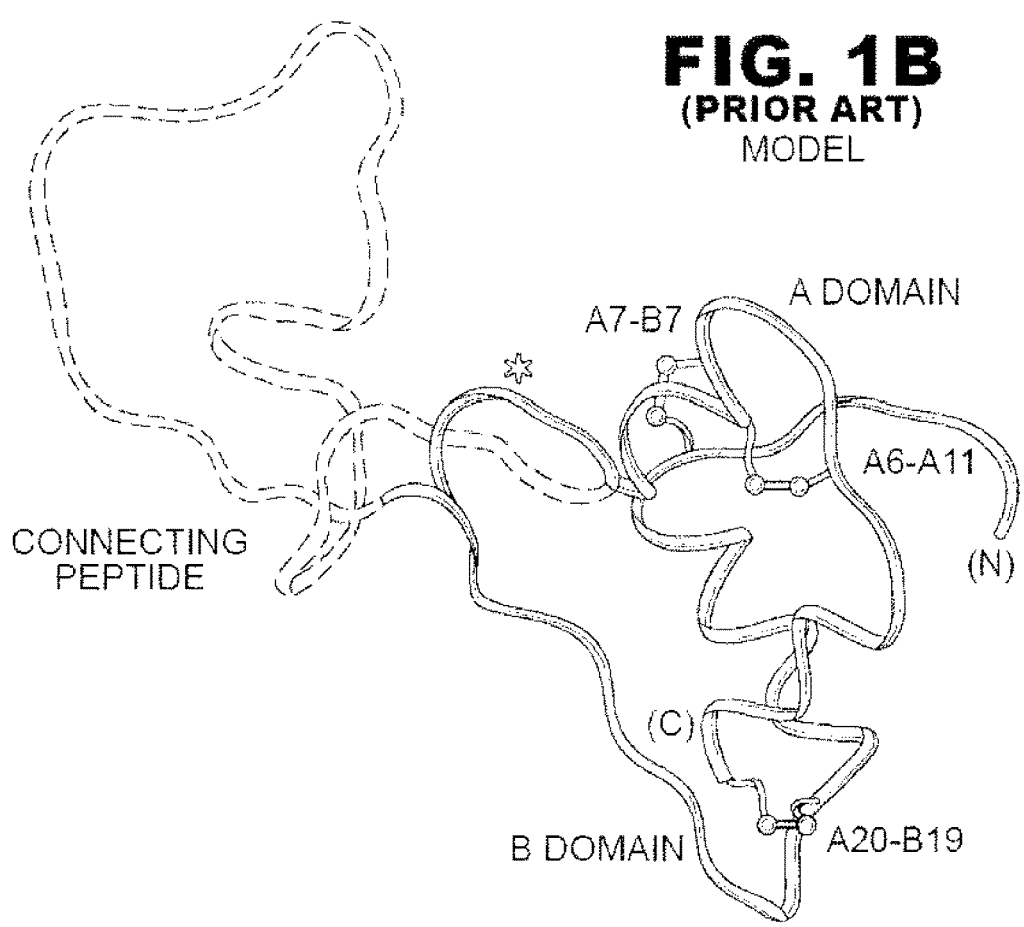
FIG. 1B is a structural model of proinsulin, consisting of an insulin-like moiety and a disordered connecting peptide (dashed line).
Figure 1C:
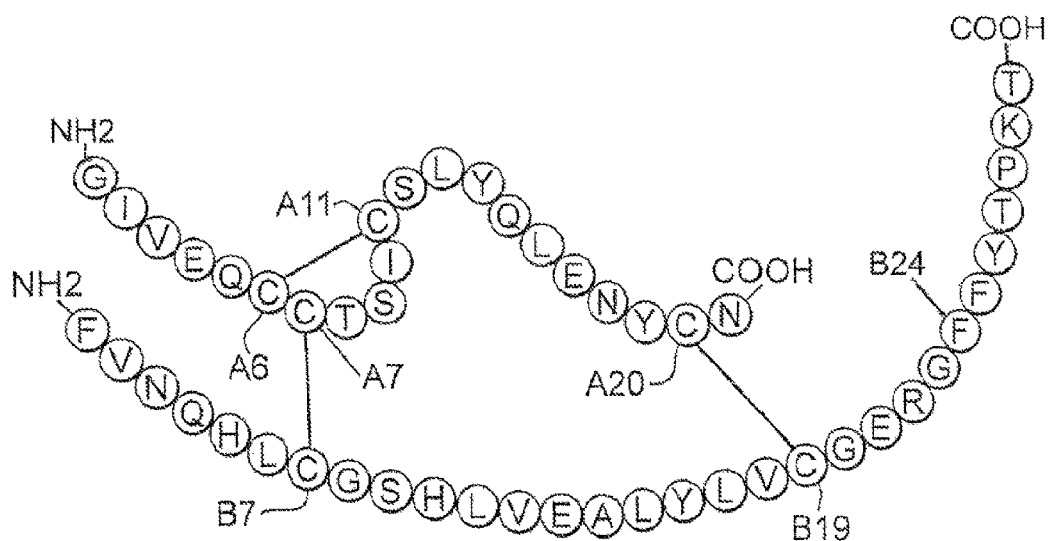
FIG. 1C is a schematic representation of the sequence of human insulin indicating the position of residue B24 in the B-chain. The top sequence is insulin A-chain which is SEQ ID NO: 2 and the bottom sequence is insulin B-chain which is SEQ ID NO: 3.
Figure 1D:
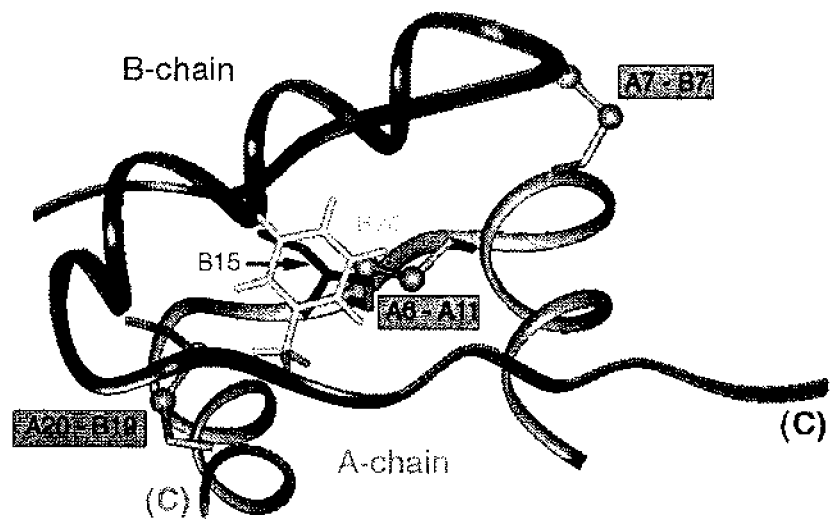
FIG. 1D is a ribbon model of an insulin monomer showing aromatic residue of Phe$^{B24}$ in relation to the three disulfide bridges. The adjoining side chains of Leu$^{B15}$ (arrow) and Phe$^{B24}$ are shown. The A- and B-chain chains are otherwise shown in light and dark gray, respectively, and the sulfur atoms of cysteines as circles.
Figure 1E:
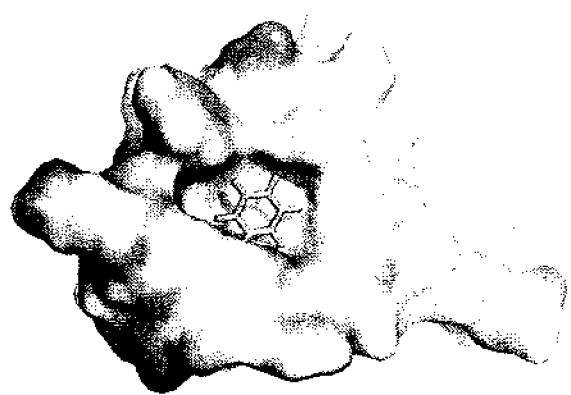
FIG. 1E is a space-filling model of insulin showing the Phe$^{B24}$ side chain within a pocket at the edge of the hydrophobic core.

The phenylalanine at B24 is an invariant amino acid in functional insulin and contains an aromatic side chain. The biological importance of Phe$^{B24}$ in insulin is indicated by a clinical mutation (Ser$^{B24}$) causing human diabetes mellitus. As illustrated in FIGS. 1D and 1E, and while not wishing to be bound by theory, Phe$^{B24}$ is believed to pack at the edge of a hydrophobic core at the classical receptor binding surface. The models are based on a crystallographic protomer (2-Zn molecule 1; Protein Databank identifier 4INS). Lying within the C-terminal β-strand of the B-chain (residues B24-B28), Phe$^{B24}$ adjoins the central α-helix (residues B9-B19). In the insulin monomer one face and edge of the aromatic ring sit within a shallow pocket defined by Leu$^{B15}$ and Cys$^{B19}$; the other face and edge are exposed to solvent (FIG. 1E). This pocket is in part surrounded by main-chain carbonyl and amide groups and so creates a complex and asymmetric electrostatic environment with irregular and loose steric borders. In the insulin dimer, and within each of the three dimer interfaces of the insulin hexamer, the side chain of Phe$^{B24}$ packs within a more tightly contained spatial environment as part of a cluster of eight aromatic rings per dimer interface (Tyr$^{B16}$, Phe$^{B24}$, Phe$^{B25}$, Tyr$^{B26}$ and their dimer-related mates). Irrespective of theory, substitution of the aromatic ring of Phe$^{B24}$ by a cyclic aliphatic ring of the same number of carbon atoms, but differing in its volume, stereo-electronic properties, and lack of planarity, provides an opportunity to preserve general hydrophobic packing within the dimer interface of the insulin hexamer while imposing distinct spatial packing constraints and perturbing the asymmetric electrostatic environment of the wild-type aromatic ring.

The present invention pertains to a non-standard modification at position B24 to improve the properties of insulin or insulin analogues with respect to rapidity of absorption following subcutaneous injection. In one instance the non-standard amino acid lacks aromaticity and its associated asymmetric distribution of partial positive and negative charges as demonstrated by substitution of the non-planar aliphatic ring system of Cyclohexanylalanine. Loss of planarity in a non-aromatic ring system is associated with a change in topographical contours and an increase in side-chain volume (FIG. 2B) relative to phenylalanine (FIG. 2A). In other instances the non-standard amino-acid substitution at B24 is accompanied by a non-standard substitution at position B29 or by three or fewer standard substitutions elsewhere in the A- or B chains.

It is envisioned that the substitutions of the present invention may be made in any of a number of existing insulin analogues. For example, the cyclic aliphatic side chain (Cha) substitution at position B24 provided herein may be made in insulin analogues such as insulin Lispro ([Lys$^{B28}$, Pro$^{B29}$]-insulin, herein abbreviated KP-insulin), insulin Aspart (Asp$^{B28}$-insulin), other modified insulins or insulin analogues, or within various pharmaceutical formulations, such as regular insulin, NPH insulin, lente insulin or ultralente insulin, in addition to human insulin. Insulin Aspart contains an Asp$^{B28}$ substitution and is sold as Nova-log® whereas insulin Lispro contains Lys$^{B28}$ and Pro$^{B29}$ substitutions and is known as and sold under the name Humalog®. These analogues are described in U.S. Pat. Nos. 5,149,777 and 5,474,978, the disclosures of which are hereby incorporated by reference herein. These analogues are each known as fast-acting insulins.

The amino-acid sequence of human proinsulin is provided, for comparative purposes, as SEQ ID NO: 1.

(human proinsulin)
SEQ ID NO: 1
Phe-Val-Asn-Gln-His-Leu-Cys-Gly-Ser-His-Leu-Val- Glu-Ala-Leu-Tyr-Leu-Val-Cys-Gly-Glu-Arg-Gly-Phe- Phe-Tyr-Thr-Pro-Lys-Thr-Arg-Arg-Glu-Ala-Glu-Asp- Leu-Gln-Val-Gly-Gln-Val-Glu-Leu-Gly-Gly-Gly-Pro- Gly-Ala-Gly-Ser-Leu-Gln-Pro-Leu-Ala-Leu-Glu-Gly- Ser-Leu-Gln-Lys-Arg-Gly-Ile-Val-Glu-Gln-Cys-Cys- Thr-Ser-Ile-Cys-Ser-Leu-Tyr-Gln-Leu-Glu-Asn-Tyr- Cys-Asn The amino-acid sequence of the A chain of human insulin is provided as SEQ ID NO: 2.

(human A chain)
SEQ ID NO: 2
Gly-Ile-Val-Glu-Gln-Cys-Cys-Thr-Ser-Ile-Cys-Ser-

Leu-Tyr-Gln-Leu-Glu-Asn-Tyr-Cys-Asn

The amino-acid sequence of the B chain of human insulin is provided as SEQ ID NO:

(human B chain)
SEQ ID NO: 3
Phe-Val-Asn-Gln-His-Leu-Cys-Gly-Ser-His-Leu-Val-

Glu-Ala-Leu-Tyr-Leu-Val-Cys-Gly-Glu-Arg-Gly-Phe-

Phe-Tyr-Thr-Pro-Lys-Thr

The amino-acid sequence of a B chain of human insulin may be modified with a substitution of a Cyclohexanylalanine (Cha) at position B24. An example of such a sequence is provided as SEQ. ID. NO 4.

SEQ ID NO: 4
Phe-Val-Asn-Gln-His-Leu-Cys-Gly-Ser-Xaa$_4$-Leu-Val-

Glu-Ala-Leu-Tyr-Leu-Val-Cys-Gly-Glu-Arg-Gly-Xaa$_1$-

Phe-Tyr-Thr-Xaa$_2$-Xaa$_3$-Thr
[Xaa$_1$ is Cha; Xaa$_2$ is Asp, Pro, Lys, or Arg; Xaa$_3$ is Lys, Pro, or Ala; and Xaa$_4$ is His or Asp]

Substitution of a Cha at position B24 may optionally be combined with non-standard substitutions at position B29 as provided in SEQ. ID. NO 5.

SEQ ID NO: 5
Phe-Val-Asn-Gln-His-Leu-Cys-Gly-Ser-Xaa$_3$-Leu-Val-

Glu-Ala-Leu-Tyr-Leu-Val-Cys-Gly-Glu-Arg-Gly-Xaa$_1$-

Phe-Tyr-Thr-Pro-Xaa$_2$-Thr
[Xaa$_1$ is Cha; Xaa$_2$ is Asp, Pro; Xaa$_2$ is Ornithine, -continued
Diaminobutyric acid, Diaminoproprionic acid,
Norleucine, Aminobutric acid, or Aminoproprionic
acid; and Xaa₃ is His or Asp]

Further combinations of other substitutions are also within the scope of the present invention. It is also envisioned that the substitutions and/or additions of the present invention may also be combined with substitutions of prior known insulin analogues. For example, the amino-acid sequence of an analogue of the B chain of human insulin containing the Lys$^{B28}$ and Pro$^{B29}$ substitutions of insulin Lispro, in which the Cha$^{B24}$ substitution may also be introduced, is provided as SEQ ID NO: 6.

SEQ ID NO: 6
Phe-Val-Asn-Gln-His-Leu-Cys-Gly-Ser-His-Leu-Val-

Glu-Ala-Leu-Tyr-Leu-Val-Cys-Gly-Glu-Arg-Gly-Xaa₁-

Phe-Tyr-Thr-Lys-Pro-Thr
[Xaa₁ is Cha]

Similarly, the amino-acid sequence of an analogue of the B chain of human insulin containing the Asp$^{B28}$ substitution of insulin Aspart, in which the Cha$^{B24}$ substitution may also be introduced, is provided as SEQ ID NO: 7.

SEQ ID NO: 7
Phe-Val-Asn-Gln-His-Leu-Cys-Gly-Ser-His-Leu-Val-

Glu-Ala-Leu-Tyr-Leu-Val-Cys-Gly-Glu-Arg-Gly-Xaa₁-

Phe-Tyr-Thr-Asp-Lys-Thr
[Xaa₁ is Cha]

A Cha$^{B24}$ substitution may also be introduced in combination with other insulin analogue substitutions such as analogues of human insulin containing His substitutions at residues A4, A8 and/or B1 as described more fully in co-pending International Application No. PCT/US07/00320 and U.S. application Ser. No. 12/160,187, the disclosures of which are incorporated by reference herein. For example, the Cha$^{B24}$ substitution may be present with His$^{A8}$ and/or His$^{B1}$ substitutions in a single-chain insulin analogue or proinsulin analogue having the amino-acid sequence represented by SEQ ID NO: 8, SEQ ID NO: 8
Xaa₁-Val-Asn-Gln-His-Leu-Cys-Gly-Ser-His-Leu-Val- Glu-Ala-Leu-Tyr-Leu-Val-Cys-Gly-Glu-Arg-Gly-Xaa₈-

Phe-Xaa₂-Thr-Xaa₃-Xaa₄-Thr-Xaa₅-Gly-Ile-Val-Xaa₆-

Gln-Cys-Cys-Xaa7-Ser-Ile-Cys-Ser-Leu-Tyr-Gln-Leu-

Glu-Asn-Tyr-Cys-Asn;

wherein Xaa₁ is His or Phe; wherein Xaa₂ is Tyr or Phe, Xaa₃ is Pro, Lys, or Asp; wherein Xaa₄ is Lys or Pro; wherein Xaa₆ is His or Glu; wherein Xaa₇ is His or Thr; wherein Xaa₅ is 0-35 of any amino acid or a break in the amino-acid chain; and wherein Xaa₈ is Cha; and further wherein at least one substitution selected from the group of the following amino-acid substitutions is present:
  Xaa₁ is His; and
  Xaa₇ is His; and
  Xaa₆ and Xaa₇ together are His.
A Cyclohexanylalanine substitution at B24 and/or two amino acid addition may also be introduced into a single-chain insulin analogue as disclosed in co-pending U.S. patent application Ser. No. 12/419,169, the disclosure of which is incorporated by reference herein.

In still another embodiment, the B-chain insulin analogue polypeptide contains a Lysine at position B3, Glutamic acid at position B29, and Cyclohexanylalanine at position B24 as provided as SEQ ID NO: 9.

SEQ ID NO: 9
Phe-Val-Lys-Gln-His-Leu-Cys-Gly-Ser-His-Leu-Val-

Glu-Ala-Leu-Tyr-Leu-Val-Cys-Gly-Glu-Arg-Gly-Xaa₁-

Phe-Tyr-Thr-Pro-Glu-Thr.

Wherein Xaa₁ is Cyclohexanylalanine.

Cyclohexanylalanine was introduced within an engineered insulin monomer of native activity, designated KP-insulin, which contains the substitutions Lys$^{B28}$ (K) and Pro$^{B29}$ (P). These two substitutions on the surface of the B-chain are believed to impede formation of dimers and hexamers but be compatible with hexamer assembly in the presence of zinc ions and a phenolic preservative. KP-insulin is the active ingredient of Humalog®, currently in clinical use as a rapid-acting insulin analogue formulation. The sequence of the B-chain polypeptide for this variant of KP-insulin is provided as SEQ ID NO: 6. Cyclohexanylalanine was also introduced at position B24 (SEQ ID NO: 21), and separately at position B25 (SEQ ID NO: 22) as a control analogue, within an engineered insulin monomer of enhanced activity, designated DKP-insulin, which contains the substitution Asp$^{B10}$ (D) in addition to the KP substitutions Lys$^{B28}$ (K) and Pro$^{B29}$ (P) in accordance with the general scheme provided in SEQ. ID. NO 4. Cha$^{B24}$ was also introduced into non-standard human insulin analogues containing either Ornithine or Norleucine at position B29 in accordance with the general scheme provided in SEQ. ID. NO 5.

Analogues of KP-insulin and DKP-insulin were prepared by trypsin-catalyzed semi-synthesis and purified by high-performance liquid chromatography (Mirmira, R. G., and Tager, H. S., 1989. *J. Biol. Chem.* 264: 6349-6354.) This protocol employs (i) a synthetic octapeptide representing residues (N)-GF*FYTKPT (including modified residue (F*) and "KP" substitutions (underlined); SEQ ID NO: 12) and (ii) truncated analogue des-octapeptide[B23-B30]-insulin or, in the case of DKP-insulin analogues, Asp$^{B10}$-des-octapeptide[B23-B30]-insulin (SEQ ID NO: 10). Because the octapeptide differs from the wild-type B23-B30 sequence (GF*FYTPKT; SEQ ID NO: 11) by interchange of Pro$^{B28}$ and Lys$^{B29}$ (italics), protection of the lysine ε-amino group is not required during trypsin treatment. In brief, des-octapeptide (15 mg) and octapeptide (15 mg) were dissolved in a mixture of dimethylacetamide/1,4-butandiol/0.2 M Tris acetate (pH 8) containing 10 mM calcium acetate and 1 mM ethylene diamine tetra-acetic acid (EDTA) (35:35:30, v/v, 0.4 mL). The final pH was adjusted to 7.0 with 10 μL of N-methylmorpholine. The solution was cooled to 12° C., and 1.5 mg of TPCK-trypsin was added and incubated for 2 days at 12° C. An additional 1.5 mg of trypsin was added after 24 hr. The reaction was acidified with 0.1% trifluoroacetic acid and purified by preparative reverse-phase HPLC (C4). Mass spectrometry using matrix-assisted laser desorption/ionization time-of-flight (MALDI-TOF; Applied Biosystems, Foster City, Calif.) in each case gave expected values (not shown). The general protocol for solid-phase synthesis is as described (Merrifield et al., 1982. *Biochem-* istry 21: 5020-5031). 9-fluoren-9-yl-methoxy-carbonyl (F-moc)-protected phenylalanine analogues were purchased from Chem-Impex International (Wood Dale, Ill.).

The above protocol was also employed to prepare analogues of human insulin containing Ornithine or Norleucine at position B29 and to introduce Cha$^{B24}$ in these respective contexts. The method of preparation of these analogues exploits non-standard amino-acid substitutions at position 29 to eliminate the tryptic site ordinarily present within the C-terminal octapeptide of the B chain (i.e., between Lys$^{B29}$ and Thr$^{B30}$) while maintaining a Proline at position 28. Pro$^{B28}$ contributes to the stability of the dimer interface within the insulin hexamer, and so this method of preparation provides near-isosteric models of wild-type insulin in which other modifications may conveniently be incorporated without the need for cumbersome side-chain protection.

Circular dichroism (CD) spectra were obtained at 4° C. and/or 25° C. using an Aviv spectropolarimeter (Weiss et al., *Biochemistry* 39: 15429-15440). Samples contained ca. 25 μM DKP-insulin or analogues in 50 mM potassium phosphate (pH 7.4); samples were diluted to 5 μM for guanidine-induced denaturation studies at 25° C. To extract free energies of unfolding, denaturation transitions were fitted by non-linear least squares to a two-state model as described by Sosnick et al., *Methods Enzymol.* 317: 393-409. In brief, CD data θ(x), where x indicates the concentration of denaturant, were fitted by a nonlinear least-squares program according to $$\theta(x) = \frac{\theta_A + \theta_B e^{\left(-\Delta G_{H_2O}^o - mx\right)/RT}}{1 + e^{-\left(\Delta G_{H_2O}^o - mx\right)/RT}}$$

where x is the concentration of guanidine and where $\theta_A$ and $\theta_B$ are baseline values in the native and unfolded states. Baselines were approximated by pre- and post-transition lines $\theta_A(x)=\theta_A^{H_2O}+m_A x$ and $\theta_B(x)=\theta_B^{H_2O}+m_B x$. The m values obtained in fitting the variant unfolding transitions are lower than the m value obtained in fitting the wild-type unfolding curve. To test whether this difference and apparent change in $\Delta G_u$ result from an inability to measure the CD signal from the fully unfolded state, simulations were performed in which the data were extrapolated to plateau CD values at higher concentrations of guanidine; essentially identical estimates of $\Delta G_u$ and m were obtained.

Figure 4:
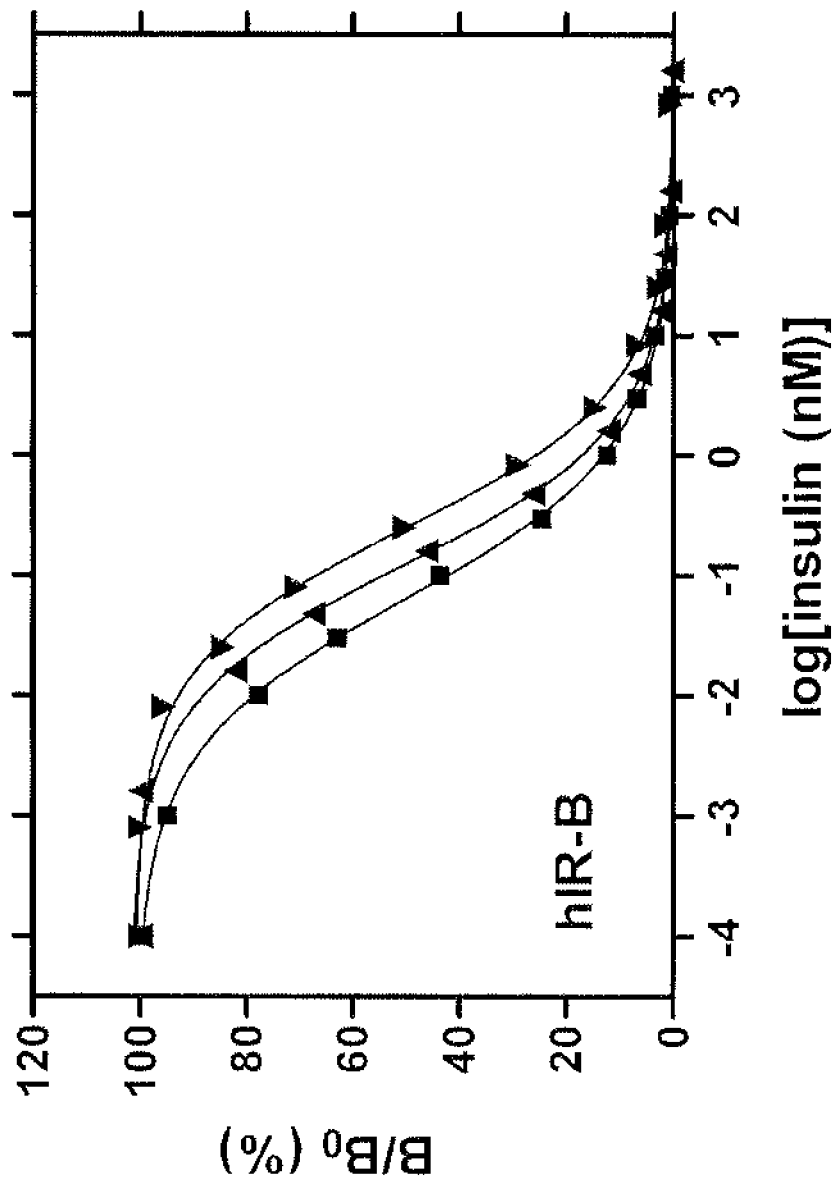
FIG. 4 is a graph showing the results of receptor-binding studies of insulin analogues. Relative activities for the B isoform of the insulin receptor (IR-B) are determined by competitive binding assay in which receptor-bound $^{125}$I-labeled human insulin is displaced by increasing concentrations of human insulin (●) or its analogues: KP-insulin (▲) and Cha$^{B24}$-KP-insulin (▼).

Relative activity is defined as the ratio of the hormone-receptor dissociation constants of analogue to wild-type human insulin, as measured by a competitive displacement assay using $^{125}$I-human insulin. Microtiter strip plates (Nunc Maxisorb) were incubated overnight at 4° C. with AU5 IgG (100 μl/well of 40 mg/ml in phosphate-buffered saline). Binding data were analyzed by a two-site sequential model. Data were corrected for nonspecific binding (amount of radioactivity remaining membrane associated in the presence of 1 μM human insulin. In all assays the percentage of tracer bound in the absence of competing ligand was less than 15% to avoid ligand-depletion artifacts. Representative data are provided in FIG. 4.

To assess hypoglycemic potencies of KP-insulin (or DKP-insulin) analogues relative to KP-insulin or wild-type insulin in vivo, male Lewis rats (mean body mass ~300 grams) were rendered diabetic by treatment with streptozotocin. (This model provides a probe of potency but not degree of acceleration of pharmacokinetics as (i) wild-type insulin, KP-insulin, and Asp$^{B28}$ insulin exhibit similar patterns of effects of blood glucose concentration and (ii) these patterns are unaffected by the presence of absence of zinc ions in the formulation at a stoichiometry sufficient to ensure assembly of insulin hexamers.) Protein solutions containing wild-type human insulin, insulin analogues, or buffer alone (protein-free sterile diluent obtained from Eli Lilly and Co.; composed of 16 mg glycerin, 1.6 mg meta-cresol, 0.65 mg phenol, and 3.8 mg sodium phosphate PH 7.4) were injected subcutaneously, and resulting changes in blood glucose were monitored by serial measurements using a clinical glucometer (Hypoguard Advance Micro-Draw meter). To ensure uniformity of formulation, insulin analogues were each re-purified by reverse-phase high-performance liquid chromatography (rp-HPLC), dried to powder, dissolved in diluent at the same maximum protein concentration (300 μg/mL) and re-quantitative by analytical C4 rp-HPLC; dilutions were made using the above buffer. Rats were injected subcutaneously at time t=0 with 20 μg insulin in 100 μl of buffer per 300 g rat. This dose corresponds to ca. 67 μg/kg body weight, which corresponds in international units (IU) to 2 IU/kg body weight. Dose-response studies of KP-insulin indicated that at this dose a near-maximal rate of glucose disposal during the first hour following injection was achieved. Five rats were studied in the group receiving Cha$^{B24}$-KP-insulin (SEQ ID NOS: 2 and 6), and five different rats were studied in the control group receiving KP-insulin (SEQ ID NOS: 2 and 20); these rats were randomly selected from a colony of 30 diabetic rats. The two groups exhibited similar mean blood glucose concentrations at the start of the experiment. Blood was obtained from clipped tip of the tail at time 0 and every 10 minutes up to 90 min. The efficacy of insulin action to reduce blood glucose concentration was calculated using the change in concentration over time (using least-mean squares and initial region of linear fall) divided by the concentration of insulin injected. The initial rate of change in blood glucose concentration in the group receiving KP-insulin was −127.1±24.6 mg/dl/h (mean±standard error of the mean); the initial rate of change in the group receiving Cha$^{B24}$-KP-insulin was −113.5±21.7 mg/dl/h. Any differences were not statistically significant. These data thus suggest that the biological potency of Cha$^{B24}$-KP-insulin is equivalent to that of KP-insulin in a zinc hexamer formulation.

The kinetic stability of insulin analogue hexamers was assessed at 25° C. relative to that of the wild-type human insulin hexamer as a cobalt (Co$^{2+}$) complex in the presence of 2.2 cobalt ions per hexamer and 50 mM phenol in a buffer consisting of 10 Tris-HCl (pH 7.4). The assay, a modification of the procedure of Beals et al. (Birnbaum, D. T., Kilcomons, M. A., DeFelippis, M. R., & Beals, J. M. Assembly and dissociation of human insulin and Lys$^{B28}$, Pro$^{B29}$-insulin hexamers: a comparison study. *Pharm Res.* 14, 25-36 (1997)), employs optical absorbance at 500-700 nm to monitor the R$_6$-hexamer-specific d-d transitions characteristic of tetrahedral cobalt ion coordination. Although the solution at equilibrium contains a predominance of cobalt insulin hexamers or cobalt insulin analogue hexamers, this equilibrium is characterized by opposing rates of insulin assembly and disassembly. To initiate the assay, the solution is made 2 mM in ethylene-diamine-tetra-acetic acid (EDTA) to sequester free cobalt ions. The time course of decay of the R$_6$-specific absorption band on addition of EDTA provides an estimate of the rate of hexamer disassembly. Whereas wild-type insulin (SEQ ID NOS: 2 and 3) exhibited a time constant of 419±51 seconds, KP-insulin (SEQ ID NOS: 2 and 20) exhibited a time constant of 114±13 seconds in accordance with its accelerated pharmacokinatics. Strikingly, the time constant for Cha$^{B24}$-KP-insulin (SEQ ID NOS: 2 and 6) was found to be 49±5 seconds, predicting a further acceleration of pharmacokinetics in human patients. Stated differently, Cha$^{B24}$-KP-insulin is almost as accelerated in its disassembly relative to KP-insulin, as KP-insulin is accelerated relative to wild type human insulin.

The far-ultraviolet circular dichroism (CD) spectrum of the Cha$^{B24}$ analogue is similar to those of the parent analogues. Modified B24 residues were introduced within the context of KP-insulin (SEQ ID NO: 6), DKP-insulin (SEQ ID NO: 21), and non-standard analogues of human insulin in which Lys$^{B29}$ was substituted by Ornithine or Norleucine (SEQ ID NO: 5). Activity values shown are based on ratio of hormone-receptor dissociation constants relative to human insulin; the activity of human insulin is thus 1.0 by definition. Standard errors in the activity values were in general less than 25%. Free energies of unfolding ($\Delta G_u$) at 25° C. were estimated based on a two-state model as extrapolated to zero denaturant concentration. Lag time indicates time (in days) required for initiation of protein fibrillation on gentle agitation at 30° C. in zinc-free phosphate-buffered saline (pH 7.4).

The baseline thermodynamic stability of KP-insulin, as inferred from a two-state model of denaturation at 25° C., is 3.0±0.1 kcal/mole. CD-detected guanidine denaturation studies indicate that the Cha$^{B24}$ substitution is associated with a small decrement in thermodynamic stability in the context of KP-insulin ($\Delta\Delta G_u$ 0.3±0.2 kcal/mole) and in the context of DKP-insulin ($\Delta\Delta G_u$ 0.4±0.2 kcal/mole). Nonetheless, the physical stability of the Cha$^{B24}$ KP analogue was found to be similar to or greater than that of KP-insulin as evaluated in triplicate during incubation in 300 µM phosphate-buffered saline (PBS) at pH 7.4 at 30° C. under gentle agitation. The samples were observed for 20 days or until signs of precipitation or frosting of the glass vial were observed. Whereas the three tubes of KP-insulin became cloudy in 10, 13, and 16 days, respectively, the three tubes of Cha$^{B24}$-KP-insulin became cloudy in 13, 15, and 20 days. These data exhibit a trend toward greater resistance to physical degradation by the Cha$^{B24}$ analogue.

Dissociation constants ($K_d$) were determined as described by Whittaker and Whittaker (2005. *J. Biol. Chem.* 280: 20932-20936), by a competitive displacement assay using $^{125}$I-Tyr$^{A14}$ insulin (kindly provided by Novo-Nordisk) and the purified and solubilized insulin receptor (isoform B or A) in a microtiter plate antibody capture assay with minor modification; transfected receptors were tagged at their C-terminus by a triple repeat of the FLAG epitope (DYKDDDDK; SEQ ID NO:23) and microtiter plates were coated by anti-FLAG M2 monoclonal antibody (Sigma). The percentage of tracer bound in the absence of competing ligand was less than 15% to avoid ligand-depletion artifacts. Binding data were analyzed by non-linear regression using a heterologous competition model (Wang, 1995, *FEBS Lett.* 360: 111-114) to obtain dissociation constants. Results are provided in Table 1 (Cha$^{B24}$ KP-insulin analogue relative to KP-insulin) and Table 2 (Cha$^{B25}$-DKP-insulin relative to DKP-insulin); dissociation constants are provided in units of nanomolar. (The two studies were conducted on different dates with different preparations of insulin receptor (IR isoform B; IR-B) and IGF receptor (IGF-1R) and so are tabulated independently.) The Cha$^{B24}$ modification of KP-insulin reduces IR-B receptor-binding affinities by between twofold and threefold; such small reductions are typically associated with native or near-native hypoglycemic potencies in vivo as demonstrated herein in diabetic Lewis rats. No significant increase was observed in the cross-binding of Cha$^{B24}$-KP-insulin to IGF-1R. The Cha$^{B24}$ modification of DKP-insulin reduces IR-B receptor-binding affinities by less than twofold; a trend toward increased cross-binding to IGF-1R was observed near the limit of statistical significance. Cha$^{B24}$-DKP-insulin was not tested in rats. The affinity of Cha$^{B25}$-DKP-insulin for IR-B was markedly impaired (binding to IR-B decreased by more than tenfold) in accordance with classical structure-activity relationships in insulin. The distinct site-specific effects of a Phe→Cha substitution (well tolerated at B24 but not at B25) presumably reflect the different structural roles of these aromatic side chains at the hormone-receptor interface.

TABLE 1

Binding of Insulin Analogues to Insulin Receptor and IGF Receptor

| Protein | IR-B binding | IGF-1R binding |
|---|---|---|
| insulin | 0.045 ± 0.007 nM | 5.1 ± 0.8 nM |
| KP-insulin | 0.093 ± 0.012 nM | 5.0 ± 0.6 nM |
| Cha$^{B24}$-KP-insulin | 0.171 ± 0.022 nM | 4.3 ± 0.7 nM |

IR-B, B isoform of the insulin receptor;
IGF-1R, Type 1 IGF receptor

TABLE 2

Binding of Insulin Analogues to Insulin Receptor and IGF Receptor

| Protein | IR-B binding | IGF-1R binding |
|---|---|---|
| DKP-insulin | 0.020 ± 0.003 nM | 3.1 ± 0.51 nM |
| Cha$^{B24}$-DKP-insulin | 0.032 ± 0.005 nM | 1.4 ± 0.22 nM |
| Cha$^{B25}$-DKP-insulin | 0.350 ± 0.050 nM | ND |

IR-B, B isoform of the insulin receptor.
ND, not determined.

The binding affinities of analogues containing the non-standard amino acids Ornithine or Norleucine at position B29 were similarly tested, both with and without a Cha substitution at B24. Results are provided in Table 3 as a percentage of the binding affinity of human insulin for human insulin receptor isoform A (hIR-A), human insulin receptor isoform B (hIR-B), and human IGF receptor (hIGF-1R); asterisks indicate values indistinguishable from 100% (wild-type) given experimental error. Whereas Orn$^{B29}$ has similar binding affinities for each receptor as wild-type insulin (asterisks), Nle$^{B29}$ confers a small decrease in affinity for hIR-B and IGF-1R relative to wild type insulin. An analogue containing Orn$^{B29}$ in combination with Cha$^{B24}$, however, had decreased binding affinity for both isoforms of insulin receptor and slightly increased affinity for hIGF-1R (possibly non-significant given experimental error). The Cha$^{B24}$, Nle$^{B29}$ analogue had similar binding affinity for hIGF-1R as the Nle$^{B29}$ only analogue, but had decreased binding affinity for hIR-B. We highlight the modesty of these changes in affinity as the observed range of in vitro hIR affinities are in each case in accordance with expected in vivo hypoglycemic potencies similar to those of wild-type insulin (i.e., as tested in a rat model); similarly, the range of in vitro IGF-1R affinities are within the range of relative affinities exhibited by insulin analogs in current clinical use. These data provide evidence that substitutions Orn$^{B29}$ and Nle$^{B29}$ have utility in semi-synthetic insulin formulations intended for therapeutic use, either alone or in combination with second-site modifications such as $Cha^{B24}$.

TABLE 3

Relative Binding Affinity of Insulin Analogues to Insulin Receptor and IGF Receptor

| Protein | hIR-A binding | hIR-B binding | hIGF-1R binding |
| --- | --- | --- | --- |
| Insulin | 100 | 100 | 100 |
| $Cha^{B24}$, $Nle^{B29}$ | 50 | 36 | 62 |
| $Cha^{B24}$, $Orn^{B29}$ | 58 | 53 | 134* |
| $Nle^{B29}$ | ND | 67 | 61 |
| $Orn^{B29}$ | 95* | 105* | 115* | hIR-A, A isoform of human insulin receptor;
hIR-B, B isoform of human insulin receptor;
hIGF-1R, human IGF receptor;
ND, not determined;
percent errors are in general less than 20% of the values given.
Asterisks indicate values whose 95% confidence intervals include 100 and so may be indistinguishable from wild-type.

Figure 5A:
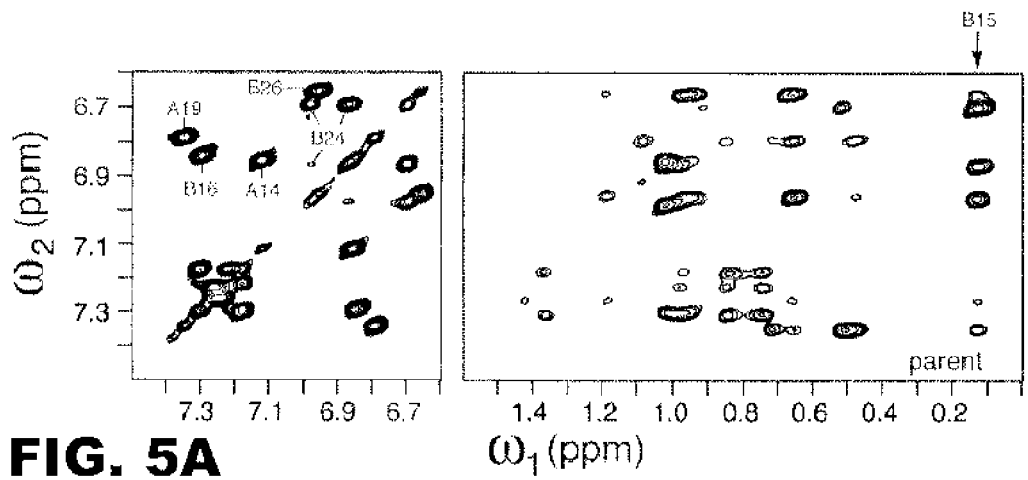
FIG. 5A provides 2D $^1$H-NMR NOESY spectra of DKP-insulin recorded at 700 MHz at 32° C. and pD 7.0.
Figure 5B:
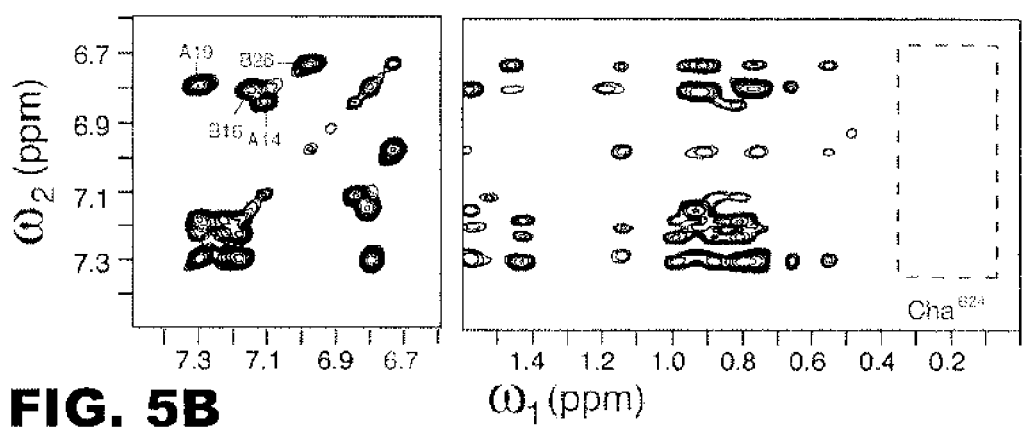
FIG. 5B provides 2D ¹H-NMR NOESY spectra of Cha$^{B24}$-DKP-insulin recorded at 700 MHz at 32° C. and pD 7.0.
Figure 5C:
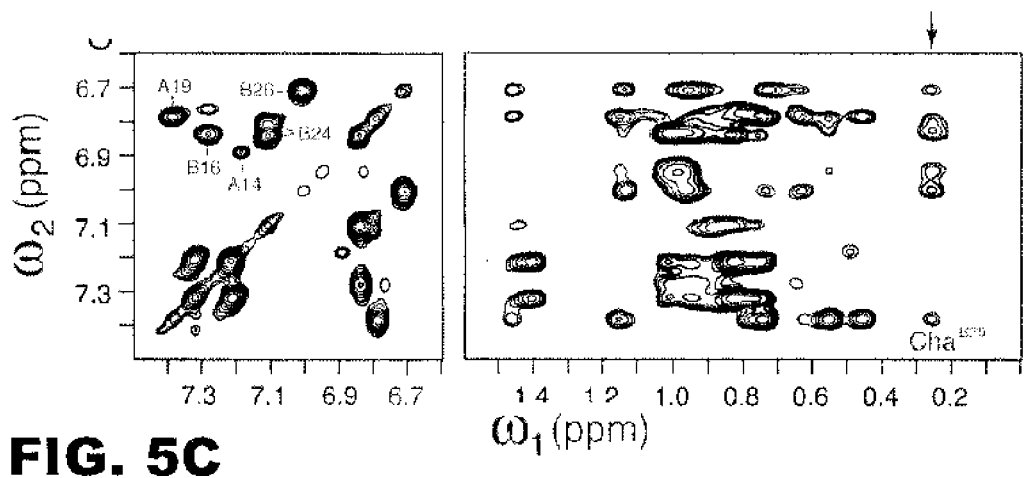
FIG. 5C provides 2D ¹H-NMR NOESY spectra of Cha$^{B25}$-DKP-insulin recorded at 700 MHz at 32° C. and pD 7.0. (Left panels) TOCSY spectrum of aromatic region. Resonance assignments are as indicated. (Right panels) NOESY spectrum providing inter-proton contacts between aromatic protons (vertical axis) and aliphatic protons (horizontal axis). Empty box in FIG. 5B highlights absence of ring-current-shifted resonances due to non-aromatic nature of Cha$^{B24}$; arrows in FIG. 5A and FIG. 5C indicate characteristic upheld shift of Leu$^{B15}$ methyl resonance due to ring current of Phe$^{B24}$. The disorder of Phe$^{B25}$ on the surface of an insulin monomer by contrast attenuates its ring-current effects.

Two-dimensional $^1$H-NMR spectra have been obtained of $Cha^{B24}$ and $Cha^{B25}$ analogues of DKP-insulin (FIG. 5). Whereas the spectrum of $Cha^{B25}$-DKP-insulin is similar to that of DKP-insulin in accordance with past studies suggesting that the ensemble-averaged aromatic ring-current effects of $Phe^{B25}$ are negligible in an insulin monomer, aliphatic substitution of $Phe^{B24}$ leads to attenuation of $Phe^{B24}$-related ring current effects. Qualitative interpretation of these spectra is nonetheless suggestive of native-like structures. Further evidence for native-like packing of $Cha^{B24}$ was provided by the crystallization of $[Cha^{B24}, Orn^{B29}]$-insulin under conditions that routinely yields crystals of wild-type zinc insulin hexamers.

Insulin analogues additionally containing a $Cha^{B24}$ substitution in a $Lys^{B28}$, $Pro^{B29}$ analogue (SEQ ID NO: 6) were created with either a wild type A-chain (SEQ ID NO: 2) or an A-chain containing a $Glu^{48}$ substitution (SEQ ID NO: 19). The results of competitive displacement assays using $^{125}$I-labeled insulin as a tracer assays for human insulin receptor isoform B and human type 1 insulin-like growth factor receptor (IGFR-1) are provided in FIGS. 6A and 6B, respectively. As shown in FIG. 6A, the affinities of $Cha^{B24}$-KP-insulin (▲) and $Glu^{48}$-$Cha^{B24}$-KP-insulin (▼) are similar to that of KP-insulin (●). Similarly, cross-binding of $Cha^{B24}$-KP-insulin and $Glu^{48}$-$Cha^{B24}$-KP-insulin to IGFR-1 is within the margin of error for that of KP insulin (FIG. 6B).

CD spectra of $Cha^{B24}$-KP-insulin and $Glu^{48}$-$Cha^{B24}$-KP-insulin resemble that of KP-insulin. 2D $^1$H-NMR spectra of $Cha^{B24}$-KP-insulin retain native-like long-range NOEs but differ in pattern of chemical shifts in accord with the loss of the $Phe^{B24}$ ring current. We measured the free energies of unfolding of $Cha^{B24}$-KP-insulin and $Glu^{48}$-$Cha^{B24}$-KP-insulin relative to KP-insulin in a zinc-free buffer at pH 7.4 and 25° C. (10 mM potassium phosphate and 50 mM KCl). This assay utilized CD detection of guanidine-induced denaturation as probed at 222 nm. Values of $\Delta G_u$ were estimated on the basis of a 2-state model. For $Cha^{B24}$-KP-insulin a possible slight decrease in stability was seen that was within experimental error ($\Delta\Delta G_u$ 0.1±0.2 kcal/mole); for $Glu^{48}$-$Cha^{B24}$-KP-insulin an increase was observed ($\Delta\Delta G_u$ 0.5±0.2 kcal/mole). This assay predicts resistance to chemical degradation similar to or greater than that of Humalog®.

The respective fibrillation lag times of KP-insulin, $Cha^{B24}$-KP-insulin and $Glu^{48}$-$Cha^{B24}$-KP-insulin under monomeric conditions at 45° C. were investigated. The proteins were made 60 µM in phosphate-buffered saline at pH 7.4 in the absence of zinc ions. Fibrillation was detected by enhancement of Thioflavin T (ThT) fluorescence and onset of cloudiness in the solution. Whereas KP-insulin (N=3 vials) formed fibrils within 2 days, $Cha^{B24}$-KP-insulin (N=3 vials) formed fibrils on day 4; solutions of $Glu^{48}$-$Cha^{B24}$-KP-insulin (N=2 vials) were formed fibrils on day 7. These data strongly suggest that the analogues provided by the claimed invention will exhibit physical stabilities at least as great as Humalog® or greater.

The EDTA sequestration assay described above was also used exploits these spectroscopic features as follows. At time t=0 a molar excess of EDTA is added to a solution of $R_6$ insulin hexamers or insulin analog hexamers. Although EDTA does not itself attack the hexamer to strip it of metal ions, any $Co^{2+}$ ions released in the course of transient hexamer disassembly become trapped by the chelator and thus unavailable for reassembly. The rate of disappearance of the blue color (the tetrahedral d-d optical transition at 574 nm of the R-specific insulin-bound $Co^{2+}$) thus provides an optical signature of the kinetics of hexamer disassembly. Respective exponential dissociation curves yield half-lives of 419±51 sec (wild-type insulin), 113±13 sec (KP-insulin), and 49±5 sec ($Cha^{B24}$-KP-insulin). These differences are dramatic. Similar findings were observed in recent studies of $Glu^{48}$-$Cha^{B24}$-KP-insulin; indeed, its half life was 50% shorter than that of $Cha^{B24}$-KP-insulin, indicating that the stabilizing A-chain substitution $Glu^{48}$ (on the hexamer surface distant from the dimer interface) does not compromise, and may further accelerate, its rate of disassembly relative to $Cha^{B24}$-KP-insulin. Because diffusion of zinc ions from the subcutaneous depot is analogous to in vitro sequestration of cobalt ions in the assay, these findings predict that $Cha^{B24}$-KP-insulin and $Glu^{48}$-$Cha^{B24}$-KP-insulin will exhibit ultra-rapid PK/PD properties.

$Cha^{B24}$-KP-insulin was tested in 2 pigs and exhibited similar potency (consistent with the rat studies) and a trend toward ultra-rapid PD. Late $t_{1/2max}$ values of 211±11 (Humalog®) and 172±13 min ($Cha^{B24}$-KP-insulin) were observed (p=0.20). Further, a 2-fold reduction was seen in the tail of insulin action (AUC above baseline infusion rate 4 mg/kg/min) between 3-5 hours post-injection which almost achieved statistical significance (p=0.07) despite the limited sample size.

An individual pig whose response to Humalog® was discovered to be unusually slow (initial time to half-maximal PD (initial $t_{1/2max}$) 81 min) was used to test the PD of the $Cha^{B24}$ analogues. Although a single individual, this pig was of potential interest as a model for the variability in PK/PD often observed among human patients in whom analogous half-maximal PD times as prolonged as 90 min have been documented. Remarkably, in this pig, $Cha^{B24}$-KP-insulin and $Glu^{48}$-$Cha^{B24}$-KP-insulin exhibited initial $t_{1/2max}$ times of 62 and 49 min, respectively; the more rapid PD of $Glu^{48}$-$Cha^{B24}$-KP-insulin is in accordance with the EDTA sequestration assay.

A method for treating a patient comprises administering an insulin analogue containing a Cha-substituted Phe or additional amino-acid substitutions in the A or B chain as known in the art or described herein. In one example, the Cha-substituted insulin analogue is an insulin analogue containing Cha at position B24 in the context of KP-insulin. In another example, $Cha^{B24}$ is substituted within human insulin analogues containing non-standard modifications at position B29 (Ornithine or Norleucine). It is yet another aspect of the present invention that use of non-standard amino-acid substitutions enables a rapid and efficient method of preparation of insulin analogues by trypsin-mediated semi-synthesis using unprotected octapeptides.

In still another example, the insulin analogue is administered by an external or implantable insulin pump. An insulin analogue of the present invention may also contain other modifications, such as a tether between the C-terminus of the B-chain and the N-terminus of the A-chain as described more fully in co-pending U.S. patent application Ser. No. 12/419,169, the disclosure of which is incorporated by reference herein.

A pharmaceutical composition may comprise such insulin analogues and which may optionally include zinc. Zinc ions may be included in such a composition at a level of a molar ratio of between 2.2 and 3.0 per hexamer of the insulin analogue. In such a formulation, the concentration of the insulin analogue would typically be between about 0.1 and about 3 mM; concentrations up to 3 mM may be used in the reservoir of an insulin pump. Modifications of meal-time insulin analogues may be formulated as described for (a) "regular" formulations of Humulin® (Eli Lilly and Co.), Humalog® (Eli Lilly and Co.), Novalin® (Novo-Nordisk), and Novalog® (Novo-Nordisk) and other rapid-acting insulin formulations currently approved for human use, (b) "NPH" formulations of the above and other insulin analogues, and (c) mixtures of such formulations.

Excipients may include glycerol, glycine, arginine, Tris, other buffers and salts, and anti-microbial preservatives such as phenol and meta-cresol; the latter preservatives are known to enhance the stability of the insulin hexamer. Such a pharmaceutical composition may be used to treat a patient having diabetes mellitus or other medical condition by administering a physiologically effective amount of the composition to the patient.

A nucleic acid comprising a sequence that encodes a polypeptide encoding an insulin analogue containing a sequence encoding at least a B-chain of insulin with a Cyclohexanylalanine at position B24 is also envisioned. This can be accomplished through the introduction of a stop codon (such as the amber codon, TAG) at position B24 in conjunction with a suppressor tRNA (an amber suppressor when an amber codon is used) and a corresponding tRNA synthetase, which incorporates a non-standard amino acid into a polypeptide in response to the stop codon, as previously described (Furter, 1998, *Protein Sci.* 7:419-426; Xie et al., 2005, *Methods.* 36: 227-238). The particular sequence may depend on the preferred codon usage of a species in which the nucleic-acid sequence will be introduced. The nucleic acid may also encode other modifications of wild-type insulin. The nucleic-acid sequence may encode a modified A- or B-chain sequence containing an unrelated substitution or extension elsewhere in the polypeptide or modified proinsulin analogues. For example, an A-chain containing a Glu$^{48}$ substitution may be utilized. The nucleic acid may also be a portion of an expression vector, and that vector may be inserted into a host cell such as a prokaryotic host cell like an *E. coli* cell line, or a eukaryotic cell line such as *S. cereviciae* or *Pischia pastoris* strain or cell line.

For example, it is envisioned that synthetic genes may be synthesized to direct the expression of a B-chain polypeptide in yeast *Piscia pastoris* and other microorganisms. The nucleotide sequence of a B-chain polypeptide utilizing a stop codon at position B24 for the purpose of incorporating a Cyclohexanylalanine at that position may be either of the following or variants thereof:

(a) with Human Codon Preferences:
(SEQ ID NO: 15)

TTTGTGAACCAACACCTGTGCGGCTCACACCTGGTGGAAGCTCTCTACCT

AGTGTGCGGGGAACGAGGCTAGTTCTACACACCCAAGACC (b) with Pichia Codon Preferences:
(SEQ ID NO: 16)
TTTGTTAACCAACATTTGTGTGGTTCTCATTTGGTTGAAGCTTTGTACTT

GGTTTGTGGTGAAAGAGGTTAGTTTTACACTCCAAAGACT

Similarly, a full length pro-insulin cDNA having human codon preferences and utilizing a stop codon at position B24 for the purpose of incorporating Cyclohexanylalanine at that position may have the sequence of SEQ. ID NO. 17.

(SEQ ID NO: 17)
TTTGTGAACC AACACCTGTG CGGCTCACAC CTGGTGGAAG

CTCTCTACCT AGTGTGCGGG GAACGAGGCT AGTTCTACAC

ACCCAAGACC CGCCGGGAGG CAGAGGACCT GCAGGTGGGG

CAGGTGGAGC TGGGCGGCGG CCCTGGTGCA GGCAGCCTGC

AGCCCTTGGC CCTGGAGGGG TCCCTGCAGA AGCGTGGCAT

TGTGGAACAA TGCTGTACCA GCATCTGCTC CCTCTACCAG

CTGGAGAACT ACTGCAACTA G

Likewise, a full-length human pro-insulin cDNA utilizing a stop codon at position B24 for the purpose of incorporating a Cyclohexanylalanine at that position and having codons preferred by *P. pastoris* may have the sequence of SEQ ID NO: 18.

(SEQ ID NO: 18)
TTTGTTAACC AACATTTGTG TGGTTCTCAT TTGGTTGAAG

CTTTGTACTT GGTTTGTGGT GAAAGAGGTT AGTTTTACAC

TCCAAAGACT AGAAGAGAAG CTGAAGATTT GCAAGTTGGT

CAAGTTGAAT TGGGTGGTGG TCCAGGTGCT GGTTCTTTGC

AACCATTGGC TTTGGAAGGT TCTTTGCAAA AGAGAGGTAT

TGTTGAACAA TGTTGTACTT CTATTTGTTC TTTGTACCAA

TTGGAAAACT ACTGTAACTA A

Other variants of these sequences, encoding the same polypeptide sequence, are possible, given the synonyms in the genetic code.

Based upon the foregoing disclosure, it should now be apparent that insulin analogues provided will carry out the objects set forth hereinabove. Namely, these insulin analogues exhibit enhanced rates of disassembly of insulin hexamers while maintaining at least a fraction of the biological activity of wild-type insulin. It is, therefore, to be understood that any variations evident fall within the scope of the claimed invention and thus, the selection of specific component elements can be determined without departing from the spirit of the invention herein disclosed and described.

The following literature is cited to demonstrate that the testing and assay methods described herein would be understood by one of ordinary skill in the art.

Furter, R., 1998. Expansion of the genetic code: Site-directed p-fluoro-phenylalanine incorporation in *Escherichia coli. Protein Sci.* 7:419-426.

Merrifield, R. B., Vizioli, L. D., and Boman, H. G. 1982. Synthesis of the antibacterial peptide cecropin A (1-33). *Biochemistry* 21: 5020-5031.

Mirmira, R. G., and Tager, H. S. 1989. Role of the phenylalanine B24 side chain in directing insulin interaction with its receptor: Importance of main chain conformation. *J. Biol. Chem.* 264: 6349-6354.

Sosnick, T. R., Fang, X., and Shelton, V. M. 2000. Application of circular dichroism to study RNA folding transitions. *Methods Enzymol.* 317: 393-409.

Wang, Z. X. 1995. An exact mathematical expression for describing competitive biding of two different ligands to a protein molecule *FEBS Lett.* 360: 111-114.

Weiss, M. A., Hua, Q. X., Jia, W., Chu, Y. C., Wang, R. Y., and Katsoyannis, P. G. 2000. Hierarchiacal protein "undesign": insulin's intrachain disulfide bridge tethers a recognition ca-helix. *Biochemistry* 39: 15429-15440.

Whittaker, J., and Whittaker, L. 2005. Characterization of the functional insulin binding epitopes of the full length insulin receptor. *J. Biol. Chem.* 280: 20932-20936.

Xie, J. and Schultz, P. G. 2005. An expanding genetic code. *Methods.* 36: 227-238.

---

What is claimed is:

1. An insulin analogue comprising the insulin B-chain polypeptide containing a Cyclohexanylalanine substitution at a position corresponding to position B24 of wild type insulin and a glutamic acid substitution at a position corresponding to position B29 of wild type insulin; wherein optionally the insulin analogue comprises a lysine substitution at a position corresponding to position B3 of wild type insulin.

2. The insulin analogue of claim 1, wherein the insulin B-chain sequence comprises SEQ ID NO: 9.

3. The insulin analogue of claim 1, wherein the insulin analogue additionally comprises the insulin A-chain polypeptide containing a Glu substitution at position A8.

4. The insulin analogue of claim 3, wherein the insulin B-chain sequence comprises SEQ ID NO: 9 and the insulin A-chain sequence comprises SEQ ID NO: 19.

* * * * *